US010232986B2

(12) United States Patent
Bucholtz et al.

(10) Patent No.: US 10,232,986 B2
(45) Date of Patent: Mar. 19, 2019

(54) VIAL WITH NON-ROUND SEAL

(71) Applicant: CSP TECHNOLOGIES, INC., Auburn, AL (US)

(72) Inventors: Michael Bucholtz, Balston Spa, NY (US); Ronald Supranowicz, Jupiter, FL (US); John Belfance, Phenix City, AL (US)

(73) Assignee: CSP TECHNOLOGIES, INC., Auburn, AL (US)

( * ) Notice: Subject to any disclaimer, the term of this patent is extended or adjusted under 35 U.S.C. 154(b) by 0 days.

(21) Appl. No.: 15/649,815

(22) Filed: Jul. 14, 2017

(65) Prior Publication Data

US 2018/0009577 A1 Jan. 11, 2018

Related U.S. Application Data

(63) Continuation of application No. 12/992,749, filed as application No. PCT/US2009/044193 on May 15, 2009.

(Continued)

(51) Int. Cl.
*B65D 43/16* (2006.01)
*G01N 33/487* (2006.01)
(Continued)

(52) U.S. Cl.
CPC ........ *B65D 43/162* (2013.01); *B01L 3/50825* (2013.01); *B65D 81/266* (2013.01);
(Continued)

(58) Field of Classification Search
CPC ............ A61B 10/0096; A61B 50/3001; A61B 2050/3008; B01L 3/50825; B01L 9/52;
(Continued)

(56) References Cited

U.S. PATENT DOCUMENTS 1,522,633 A 1/1925 Kister
2,522,952 A 9/1950 Krohn
(Continued)

FOREIGN PATENT DOCUMENTS

CN 1816483 A 9/2006
EP 1220794 3/2001
(Continued)

OTHER PUBLICATIONS

Bonenberger, Paul R., First Snap-Fit Handbook—Creating and Managing Attachments for Plastic Parts (2nd Edition), (2005). Hanser Publishers. Online version available at: http://app.knovel.com/hotlink/toc/id:kpFSFHCMA4/first-snap-fit-handbook/first-snap-fit-handbook—Excerpt from Chapter 3.

(Continued)

*Primary Examiner* — J. Gregory Pickett
*Assistant Examiner* — Gideon Weinerth
(74) *Attorney, Agent, or Firm* — David B. Gornish; Eckert Seamans Cherin & Mellott, LLC

(57) ABSTRACT

A moisture-tight, re-sealable container is disclosed having a lid and body. The lid and body have a non-round seal that is substantially moisture tight when the lid is seated on the body, admitting less than 1000 micrograms per day of water to a package. A reinforcement stiffens or reinforces at least a portion of the seal against inward deflection along an axis defined by the minor diameter when the lid is seated on the body. Optionally the reinforcement is at least one spline subdividing the reservoir. A method of making dispensers for objects of varying length to customize particular dispensers to dispense such objects of a particular length is also disclosed.

24 Claims, 18 Drawing Sheets

Related U.S. Application Data

(60) Provisional application No. 61/053,277, filed on May 15, 2008, provisional application No. 61/081,514, filed on Jul. 17, 2008.

(51) Int. Cl.

| | |
|---|---|
| *B65D 53/02* | (2006.01) |
| *B65D 25/10* | (2006.01) |
| *B65D 81/26* | (2006.01) |
| *B01L 3/00* | (2006.01) |
| *B01L 9/00* | (2006.01) |

(52) U.S. Cl.
CPC ......... *G01N 33/48778* (2013.01); *B01L 9/52* (2013.01); *B01L 2200/0689* (2013.01); *B01L 2200/141* (2013.01); *B01L 2200/142* (2013.01); *B01L 2300/043* (2013.01); *B01L 2300/0609* (2013.01); *B01L 2300/0825* (2013.01); *B01L 2300/123* (2013.01); *B65D 2543/0074* (2013.01); *B65D 2543/00148* (2013.01); *B65D 2543/00296* (2013.01); *B65D 2543/00537* (2013.01); *B65D 2543/00564* (2013.01); *B65D 2543/00629* (2013.01); *B65D 2543/00685* (2013.01); *B65D 2543/00796* (2013.01); *B65D 2543/00842* (2013.01)

(58) Field of Classification Search
CPC ......... B01L 2200/141; B01L 2200/142; B01L 2200/0689; B01L 2200/025; B01L 2200/022; B01L 2200/023; B01L 2300/043; B01L 2300/0609; B01L 2300/0825; B01L 2300/123; B42F 17/02; B42F 17/00; B65D 25/102; B65D 25/107; B65D 2543/00148; B65D 2543/00296; B65D 2543/00537; B65D 2543/00564; B65D 2543/00629; B65D 2543/00685; B65D 2543/0074; B65D 2543/00796; B65D 2543/00842; B65D 43/162; B65D 53/00; B65D 81/266; G03B 23/105; G01N 33/48778; G01N 33/487; G01N 33/48757; G01N 33/4875; Y10T 29/49826
USPC ........... 220/378, 203.18, 224, 229; 215/231; 206/443, 349; 422/565; 221/267, 309, 221/310; 312/185; 402/61
See application file for complete search history.

(56) References Cited

U.S. PATENT DOCUMENTS

| | | | |
|---|---|---|---|
| 2,727,547 A | 12/1955 | Moon, III | |
| 2,852,054 A | 9/1958 | Motley | |
| 2,958,439 A | 11/1960 | Yochem | |
| 3,063,549 A | 11/1962 | Weichselbaum | |
| 3,346,099 A | 10/1967 | Thomas et al. | |
| 3,820,309 A | 6/1974 | Cullen et al. | |
| 4,061,226 A * | 12/1977 | Essen | B65D 85/38 206/212 |
| 4,717,018 A | 1/1988 | Sacherer et al. | |
| 4,783,056 A | 11/1988 | Abrams | |
| 4,812,116 A | 3/1989 | Abrams | |
| 4,969,573 A | 11/1990 | Dupuis et al. | |
| 5,078,909 A | 1/1992 | Shigeta et al. | |
| 5,114,003 A | 5/1992 | Jackisch et al. | |
| 5,202,093 A * | 4/1993 | Cloyd | B01L 3/50825 215/247 |
| 5,277,312 A * | 1/1994 | Vumbaca | A61M 5/3205 206/365 |
| 5,505,308 A | 4/1996 | Eikmeier et al. | |
| 5,667,094 A * | 9/1997 | Rapchak | B65D 43/162 215/306 |
| 5,788,064 A * | 8/1998 | Sacherer | A61B 10/0096 206/204 |
| 5,829,581 A | 11/1998 | Wicker | |
| 5,911,937 A | 6/1999 | Hekal | |
| 5,947,274 A | 9/1999 | Taskis et al. | |
| 6,303,064 B1 | 10/2001 | Abrams et al. | |
| RE37,676 E | 4/2002 | Abrams et al. | |
| 6,376,126 B1 * | 4/2002 | Faust | H01M 2/024 429/176 |
| 6,398,067 B1 | 6/2002 | Belfance et al. | |
| 6,446,793 B1 | 9/2002 | Layshock | |
| 6,502,711 B1 * | 1/2003 | McRae | B65D 21/0204 211/71.01 |
| 6,629,616 B1 * | 10/2003 | Heinzle | A47B 47/00 211/85.7 |
| 6,705,463 B1 | 3/2004 | Bucholtz et al. | |
| 6,769,558 B1 | 8/2004 | Bucholtz | |
| 7,059,492 B2 * | 6/2006 | Giraud | B65D 43/162 220/375 |
| 7,198,161 B2 | 4/2007 | Bucholtz | |
| 7,337,918 B2 * | 3/2008 | Fowler | B65D 83/0829 221/232 |
| 7,413,083 B2 | 8/2008 | Belfance et al. | |
| 7,501,093 B2 | 3/2009 | Demelo et al. | |
| D599,032 S * | 8/2009 | Bucholtz | D24/224 |
| 7,628,292 B2 * | 12/2009 | Lancesseur | B65D 1/26 221/267 |
| 7,665,601 B2 | 2/2010 | Portier | |
| 7,670,562 B2 | 3/2010 | Sacherer | |
| 7,775,357 B2 * | 8/2010 | Clarke | A61M 5/3205 206/365 |
| D631,168 S * | 1/2011 | Bucholtz | D24/224 |
| 8,006,368 B2 | 8/2011 | Logel et al. | |
| 8,225,928 B2 * | 7/2012 | Perrier | A45C 11/00 206/305 |
| 8,236,254 B2 | 8/2012 | Myles et al. | |
| 8,685,346 B2 | 4/2014 | Logel et al. | |
| 8,844,725 B2 * | 9/2014 | Chan | B65D 25/102 206/305 |
| 2002/0088814 A1 | 7/2002 | Belfance et al. | |
| 2003/0133847 A1 * | 7/2003 | Hagen | G01N 33/48757 422/430 |
| 2004/0007585 A1 | 1/2004 | Griffith et al. | |
| 2004/0031712 A1 | 2/2004 | Maxim et al. | |
| 2004/0154941 A1 | 8/2004 | Montler | |
| 2004/0173488 A1 | 9/2004 | Griffin et al. | |
| 2005/0016873 A1 | 1/2005 | Belfance et al. | |
| 2005/0218024 A1 * | 10/2005 | Lang | A61B 50/3001 206/438 |
| 2007/0080093 A1 * | 4/2007 | Boozer | B65D 43/021 206/569 |
| 2007/0084735 A1 | 4/2007 | Lancesseur et al. | |
| 2007/0084749 A1 | 4/2007 | Demelo et al. | |
| 2007/0170202 A1 * | 7/2007 | Chen | A45C 11/00 221/267 |
| 2007/0193891 A1 | 8/2007 | Portier | |
| 2007/0196240 A1 * | 8/2007 | Boozer | G01N 33/48757 422/400 |
| 2008/0257905 A1 | 10/2008 | Giraud et al. | |
| 2010/0000905 A1 * | 1/2010 | Wang | B65D 83/02 206/569 |
| 2010/0140116 A1 * | 6/2010 | Stiene | B65D 81/266 206/204 |
| 2011/0056951 A1 * | 3/2011 | Wooldridge | B65D 81/267 220/495.01 |
| 2011/0127175 A1 | 6/2011 | Chan et al. | |
| 2011/0127176 A1 * | 6/2011 | Chang | B65D 43/162 206/204 |
| 2011/0146420 A1 * | 6/2011 | Okada | B01L 3/5021 73/864.51 |
| 2011/0174644 A1 * | 7/2011 | Chan | B65D 25/102 206/305 |
| 2011/0182785 A1 * | 7/2011 | Chan | G01N 33/48757 422/565 |

(56) References Cited

U.S. PATENT DOCUMENTS

| | | | | |
|---|---|---|---|---|
| 2011/0210021 | A1* | 9/2011 | Logel | G01N 33/48778 206/223 |
| 2011/0226643 | A1* | 9/2011 | Kates | A61B 5/14532 206/305 |
| 2011/0247949 | A1 | 10/2011 | Yao | |
| 2012/0080330 | A1* | 4/2012 | Rush | B65D 1/24 206/305 |
| 2012/0082597 | A1* | 4/2012 | Doniger | B01L 3/5023 422/401 |
| 2012/0193246 | A1* | 8/2012 | Chang | B65D 43/162 206/204 |
| 2012/0199601 | A1* | 8/2012 | Sawa | G01N 33/48757 221/1 |
| 2013/0220844 | A1* | 8/2013 | Logel | B65D 81/265 206/204 |
| 2014/0299623 | A1* | 10/2014 | Giraud | B65D 83/0864 221/279 |
| 2014/0319149 | A1* | 10/2014 | Freedman | B65D 25/04 220/528 |
| 2014/0367286 | A1* | 12/2014 | Chen | B65D 85/38 206/305 |
| 2016/0001927 | A1* | 1/2016 | Lucas, Jr. | B65D 25/02 206/204 |
| 2016/0031627 | A1* | 2/2016 | Yeh | B65D 81/266 206/204 |
| 2016/0130045 | A1* | 5/2016 | Giraud | B65D 43/162 53/492 |
| 2017/0108486 | A1* | 4/2017 | Joseph | G01N 33/48778 |
| 2018/0016081 | A1* | 1/2018 | Schneider | B65D 81/266 |

FOREIGN PATENT DOCUMENTS

| | | |
|---|---|---|
| FR | 2623696 A1 | 6/1989 |
| JP | H09012064 A | 1/1997 |
| JP | H0937839 A | 2/1997 |
| JP | 2006502062 A | 1/2006 |
| JP | 2007504063 A | 3/2007 |
| KR | 100487466 B1 | 5/2005 |
| WO | 9633108 A1 | 10/1996 |
| WO | 0115989 A1 | 3/2001 |
| WO | 0194240 A1 | 12/2001 |
| WO | 2004033339 A1 | 4/2004 |
| WO | 2005026013 A2 | 3/2005 |
| WO | 2006108156 A2 | 10/2006 |
| WO | 2009140627 A2 | 11/2009 |

OTHER PUBLICATIONS

Canadian Office Action dated May 19, 2015 issued in application No. 2,724,353.
Canadian Office Action dated Feb. 24, 2016 issued in application No. 2,724,353.
Chinese Office Action dated Aug. 18, 2011 issued in application No. 200980117472.2.
Chinese Office Action dated Jan. 6, 2014 issued in application No. 201210057738.2.
Chinese Office Action dated Aug. 22, 2014 issued in application No. 201210057738.2.
Chinese Office Action dated Mar. 4, 2015 issued in application No. 201210057738.2.
European Search Report dated May 4, 2011 issued in application No. 09747708.7.
European Communication pursuant to Article 94(3) EPC dated Apr. 12, 2012 issued in application No. 09747708.7.
European Search Report dated Jul. 16, 2018 issued in application No. 18159389.8.
European Search Report dated Sep. 25, 2018 issued in application No. 18180101.0.
Japanese Notice of Reason(s) for Rejection dated Mar. 28, 2013 issued in application No. 2011-509764.
Japanese Notice of Reason(s) for Rejection dated Jul. 7, 2014 issued in application No. 2011-509764.
Japanese Notice of Reason(s) for Rejection dated Mar. 16, 2015 issued in application No. 2011-509764.
Japanese Notice of Reason(s) for Rejection dated May 31, 2016 issued in application No. 2015-145975.
Japanese Notice of Reason(s) for Rejection dated Jan. 24, 2017 issued in application No. 2015-145975.
International Preliminary Report on Patentability dated Nov. 17, 2010 relating to PCT/US2009/044193.
International Search Report dated Dec. 30, 2009 relating to PCT/US2009/044193.
Written Opinion dated Dec. 30, 2009 relating to PCT/US2009/044193.

* cited by examiner

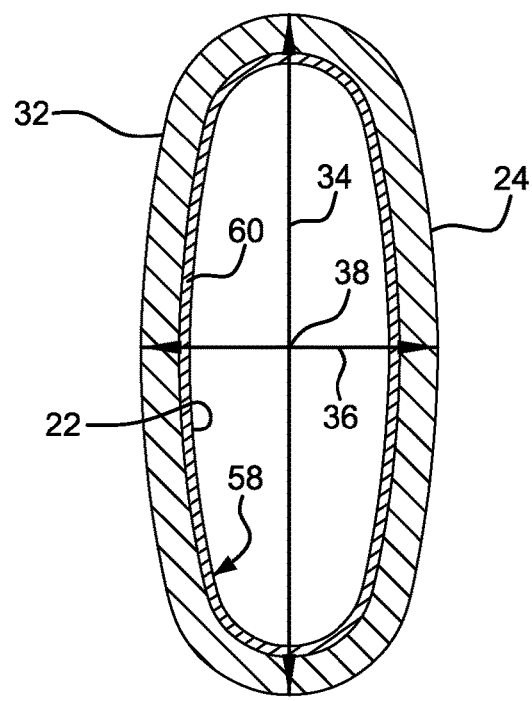
FIG. 3
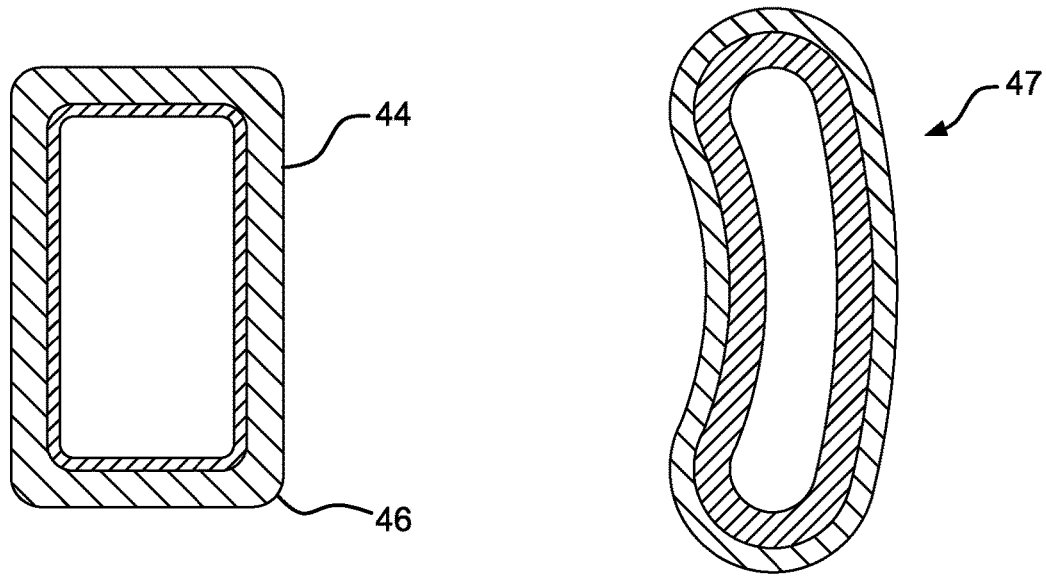
FIG. 5                    FIG. 6

VIAL WITH NON-ROUND SEAL

This application claims the priority of U.S. Ser. Nos. 61/053,277, filed May 15, 2008, and 61/081,514, filed Jul. 17, 2008. These two entire patent applications are incorporated here by reference.

BACKGROUND

The present disclosure relates to containers that can be used, for example, to house test strips, pills, capsules, particulate materials, liquids, or other objects or materials and control the ingress and/or egress of moisture. This patent application discloses technology related to that of U.S. Ser. No. 29/318,272, filed May 16, 2008. That patent application is incorporated here by reference.

Cylindrical containers are described in the following patents as being "leak-proof:" U.S. Pat. Nos. 4,783,056, 4,812,116, RE 37,676 and 6,303,064. U.S. Pat. Nos. 6,769,558 and 7,198,161 and European patent 1 220 794, all to the present inventor, disclose a leakproof, resealable cylindrical container and cap assembly. The disclosure of the processes of producing injection molded plastic containers and sealing them are incorporated by reference herein.

SUMMARY

An aspect of the invention is a moisture proof, resealable non-cylindrical container and lid assembly. The term "resealable" means that the closure can be closed at least once after the container is opened for the first time. Preferably, the closure can be opened and closed additional times after the initial opening to remove all of the contents.

The container has a body having an interior space, defined by a generally tubular sidewall. The body has a lid, and the lid and body have a non-round seal that is substantially moisture proof when the lid is seated on the body, meaning that when sealed the container admits less than 1000 micrograms per day of water determined by a moisture ingress test method. The container optionally is sized as a pharmaceutical package enclosing between 1 and 500 ml of interior volume, alternatively between 10 and 200 ml of interior volume, alternatively between 20 and 100 ml of internal volume.

The body has a generally tubular sidewall with first and second axially opposed ends, a base, and a dispensing opening axially spaced from the base and at least adjacent to the second end. The interior space is disposed generally within the sidewall and at least generally between the base and the dispensing opening. The sidewall has a cross-section having a major diameter and a minor diameter, wherein the ratio between the major diameter and the minor diameter of the sidewall cross-section is a value between 1.1:1 and 10:1, inclusive.

The container has a non-round body sealing surface located on the body and disposed about the dispensing opening, the body sealing surface having a major diameter and a minor diameter, wherein the ratio between the major diameter and the minor diameter of the body sealing surface is a value between 1.1:1 and 10:1, inclusive.

The lid is configured to seat on the body. There is a lid sealing surface located on the lid. The body sealing surface and the lid sealing surface are configured to mate to form a seal between the lid and the body when the lid is seated on the body. The lid and lid sealing surface at least substantially close the dispensing opening and isolate the interior space from ambient conditions.

An insert communicates with the interior space of the container and reinforces at least a portion of the body sealing surface against inward deflection along an axis defined by the minor diameter when the lid is seated on the body. The container has a moisture ingress rate of the container having a moisture ingress rate of 100-1000 micrograms per day, optionally 200-700 micrograms per day, optionally 380-700 micrograms per day, optionally 400-700 micrograms per day, optionally 250-400 micrograms per day, optionally less than 300 micrograms per day, at 80% relative humidity and 72° F. (22.2° C.).

Optionally, in any embodiment above, the interior space is defined at least in part by an interior surface made of a desiccant material.

Optionally, in any embodiment above, the interior space is defined at least in part by a reinforcement stiffening the container against deflection along the minor axis.

Optionally, in any embodiment above, the reinforcement is an insert assembled with the container.

Optionally, in any embodiment above, the insert is secured to the container by an interference fit between the insert and the inner wall of the container Optionally, in any embodiment above, the insert is made of a desiccant material.

Optionally, in any embodiment above, the insert is disposed within the container.

Optionally, in any embodiment above, the insert is a liner generally following the inner wall of the container.

Optionally, in any embodiment above, at least one of the ends of the container has an interior portion made of desiccant material.

Optionally, in any embodiment above, the sidewall has an interior portion made of desiccant material.

Optionally, in any embodiment above, the lid has an interior portion made of desiccant material.

Optionally, in any embodiment above, at least a portion of the desiccant material is located in the interior space.

Optionally, in any embodiment above, at least a portion of the desiccant is a particulate material.

Optionally, in any embodiment above, at least a portion of the desiccant is provided in the form of one or more sachets.

Optionally, in any embodiment above, at least a portion of the desiccant is provided in the form of one or more canisters.

Optionally, in any embodiment above, at least a portion of the desiccant is provided in the form of one or more pellets.

Optionally, in any embodiment above, the container further comprises a sleeve of desiccant material disposed within the body and at least partially defining the interior space.

Optionally, in any embodiment above, the sleeve is integrally formed with at least one of the sidewall and an end wall.

Optionally, in any embodiment above, the container further comprises a tether linking the container body and lid.

Optionally, in any embodiment above, the tether comprises a hinge.

Optionally, in any embodiment above, the tether comprises an integral hinge.

Optionally, in any embodiment above, the hinge is configured to orient the lid to seat on the body when the lid and body are pivoted together.

Optionally, in any embodiment above, the hinge defines a pivot axis that is generally perpendicular to the major axis.

Optionally, in any embodiment above, the hinge defines a pivot axis that is generally parallel to the major axis.

Optionally, in any embodiment above, the hinge extends from the sidewall at least adjacent to the end of the major axis.

Optionally, in any embodiment above, the hinge extends from the sidewall at least adjacent to the end of the minor axis.

Optionally, in any embodiment above, the body is at least generally oval in cross-section.

Optionally, in any embodiment above, the body is at least generally polygonal in cross-section.

Optionally, in any embodiment above, the body is at least generally rectangular in cross-section.

Optionally, in any embodiment above, the body has at least one rounded corner.

Optionally, in any embodiment above, at least a portion of the dispensing opening is defined by the second end of the sidewall.

Optionally, in any embodiment above, the lid comprises a closed surface supporting the lid sealing surface.

Optionally, in any embodiment above, the lid comprises a skirt surrounding and depending from the lid sealing surface.

Optionally, in any embodiment above, the skirt is generally tubular.

Optionally, in any embodiment above, the skirt cross-section is substantially congruent to the cross-section of the body sidewall, at least substantially defining an extension of the generally tubular sidewall when the lid is seated on the body.

Optionally, in any embodiment above, the ratio between the major diameter and the minor diameter of the cross-section of the body sidewall is a value between 1.5:1 and 5:1, inclusive.

Optionally, in any embodiment above, the ratio between the major diameter and the minor diameter of the cross-section of the sidewall is a value between 1.5:1 and 4:1, inclusive.

Optionally, in any embodiment above, the ratio between the major diameter and the minor diameter of the cross-section of the sidewall is a value between 1.5:1 and 3:1, inclusive.

Optionally, in any embodiment above, the ratio between the major diameter and the minor diameter of the cross-section of the sidewall is a value between 2:1 and 5:1, inclusive.

Optionally, in any embodiment above, the ratio between the major diameter and the minor diameter of the cross-section of the sidewall is a value between 2:1 and 4:1, inclusive.

Optionally, in any embodiment above, the ratio between the major diameter and the minor diameter of the cross-section of the sidewall is a value between 2:1 and 3:1, inclusive.

Optionally, in any embodiment above, the ratio between the major diameter and the minor diameter of the cross-section of the body sidewall is a value between 1.5:1 and 5:1, inclusive.

Optionally, in any embodiment above, the ratio between the major diameter and the minor diameter of the cross-section of the body sealing surface is a value between 1.5:1 and 4:1, inclusive.

Optionally, in any embodiment above, the ratio between the major diameter and the minor diameter of the cross-section of the body sealing surface is a value between 1.5:1 and 3:1, inclusive.

Optionally, in any embodiment above, the ratio between the major diameter and the minor diameter of the cross-section of the body sealing surface is a value between 2:1 and 5:1, inclusive.

Optionally, in any embodiment above, the ratio between the major diameter and the minor diameter of the cross-section of the body sealing surface is a value between 2:1 and 4:1, inclusive.

Optionally, in any embodiment above, the ratio between the major diameter and the minor diameter of the cross-section of the body sealing surface is a value between 2:1 and 3:1, inclusive.

Optionally, in any embodiment above, at least a portion of the body and at least a portion of the lid are formed in one shot in an injection mold.

Optionally, in any embodiment above, the body and the lid are formed in two shots in an injection mold.

Optionally, in any embodiment above, the respective shots are a substantially moisture blocking polymeric material and a desiccant polymeric material.

Another embodiment of the invention is a dispenser for strips of material, comprising a generally tubular body, a first platform, a second platform, and at least one spline. The body has an interior surface and first and second axially opposed ends, at least one of the ends defining a dispensing opening. The first platform extends laterally within the interior surface and positioned at the first end or between the first and second ends of the body. The second platform extends laterally within the interior surface, is positioned between and spaced axially from the first platform and the dispensing opening, and defines a reservoir between the second platform and the dispensing opening and a region between the first and second platforms. The spline extends axially and laterally within the reservoir and subdivides the reservoir into plural axially extending reservoirs communicating with the dispensing opening.

Optionally, in any embodiment above, there is an open path of communication between the reservoir and at least one of the strip reservoirs.

Optionally, in any embodiment above, there is an open path of communication between the reservoir and each of the strip reservoirs.

Optionally, in any embodiment above, at least one open path of communication is a perforation in the second platform.

Optionally, in any embodiment above, there is a desiccant material exposed to the reservoir.

Optionally, in any embodiment above, the desiccant material is in contact with the region.

Optionally, in any embodiment above, the region is defined by an interior surface composed at least in part of a desiccant material.

Optionally, in any embodiment above, at least a portion of at least one of the body interior surface, a spline, the first platform, and the second platform is composed of a desiccant material.

Optionally, in any embodiment above, at least a portion of the body interior surface is composed of a desiccant material.

Optionally, in any embodiment above, at least a portion of at least one spline is composed of a desiccant material.

Optionally, in any embodiment above, at least a portion of the first platform is composed of a desiccant material.

Optionally, in any embodiment above, at least a portion of the second platform is composed of a desiccant material.

Optionally, in any embodiment above, the body and at least one of the first platform, the second platform, and a spline are integral.

Optionally, in any embodiment above, the body and the first platform are integral.

Optionally, in any embodiment above, the body and the second platform are integral.

Optionally, in any embodiment above, the body and a spline are integral.

Optionally, in any embodiment above, the body and each spline are integral.

Optionally, in any embodiment above, the body and each of the first platform, the second platform, and the splines are injection molded.

Optionally, in any embodiment above, at least a portion of the body and at least a portion of the first platform are formed in one shot in an injection mold.

Optionally, in any embodiment above, the second platform and splines are formed in one shot in an injection mold.

Optionally, in any embodiment above, at least a portion of the body and the first platform are formed in a first shot in an injection mold and the second platform and splines are formed in a second shot in an injection mold.

Optionally, in any embodiment above, the portions formed in the first shot define a first part, the portions formed in the second shot define a second part, and the first and second parts are joined together to define a dispenser.

Optionally, in any embodiment above, there is a desiccant disposed in the region.

Optionally, in any embodiment above, the desiccant is a particulate material.

Optionally, in any embodiment above, the desiccant is provided in the form of one or more sachets, canisters, or pellets.

Optionally, in any embodiment above, there is a cap for covering the dispensing opening.

Optionally, in any embodiment above, there is a first seal surface on the cap and a second seal surface on the body, the seal surfaces being mateable to at least substantially seal the dispensing opening.

Optionally, in any embodiment above, there is a hinge joining the dispenser body and cap.

Optionally, in any embodiment above, there is a desiccant material disposed within the cap.

Optionally, in any embodiment above, there is a sleeve of desiccant material disposed within the body and at least partially defining at least one of the reservoir and region.

Optionally, in any embodiment above, the sleeve is integrally formed with at least one of the first and second platforms.

Optionally, in any embodiment above, the second platform has a first portion defining a first strip reservoir.

Optionally, in any embodiment above, the second platform further comprises a second portion non-coplanar with the first portion defining a second strip reservoir.

Optionally, in any embodiment above, there is a second strip reservoir defined by a portion of the first platform.

Optionally, in any embodiment above, the second strip reservoir is axially longer than the first strip reservoir.

Optionally, in any embodiment above, the body is generally oval in cross-section.

Optionally, in any embodiment above, the splines lie substantially parallel to the laterally extending long axis of the oval.

Optionally, in any embodiment above, the splines lie substantially parallel to the laterally extending short axis of the oval.

Optionally, in any embodiment above, there are perpendicular laterally extending first and second axes, further comprising one or more strips of material in at least one of the reservoirs oriented with their major faces substantially parallel to the first axis.

Optionally, in any embodiment above, there are perpendicular laterally extending first and second axes, further comprising one or more strips of material in at least one of the reservoirs oriented with their major faces substantially parallel to the second axis.

Another aspect of the invention is a method of making dispensers for objects of varying length to customize particular dispensers to dispense such objects of a particular length. The method is carried out in several steps.

One step is providing a first injection mold cavity adapted to form a generally tubular body having an interior surface; first and second axially opposed ends, at least one of the ends defining a dispensing opening; and a first platform extending laterally within the interior surface and positioned between the axially opposed ends of the body.

Another step is providing a second injection mold cavity adapted to form an insert sized and configured to fit within the generally tubular body, the insert having a second platform configured to be positioned between and spaced axially from the first platform and the dispensing opening when the insert is assembled with the body, defining a reservoir between the second platform and the dispensing opening and a region between the first and second platforms.

A third step is modifying at least one of the first and second injection mold cavities to place the first and second platforms of the tubular body and the insert in relative axial positions adapted to support objects of a specific length on the second platform at a predetermined position relative to the dispensing opening.

Optionally, in any embodiment above, the second injection mold cavity is modified.

Optionally, in any embodiment above, the first injection mold cavity is not modified to customize the dispenser.

BRIEF DESCRIPTION OF DRAWINGS

FIG. 3 is a cross-section taken along section line 3-3 of FIG. 1.

FIG. 5 is a cross-section similar to FIG. 3 of another embodiment.

FIG. 6 is a cross-section similar to FIG. 3 of yet another embodiment.

Figure 1:
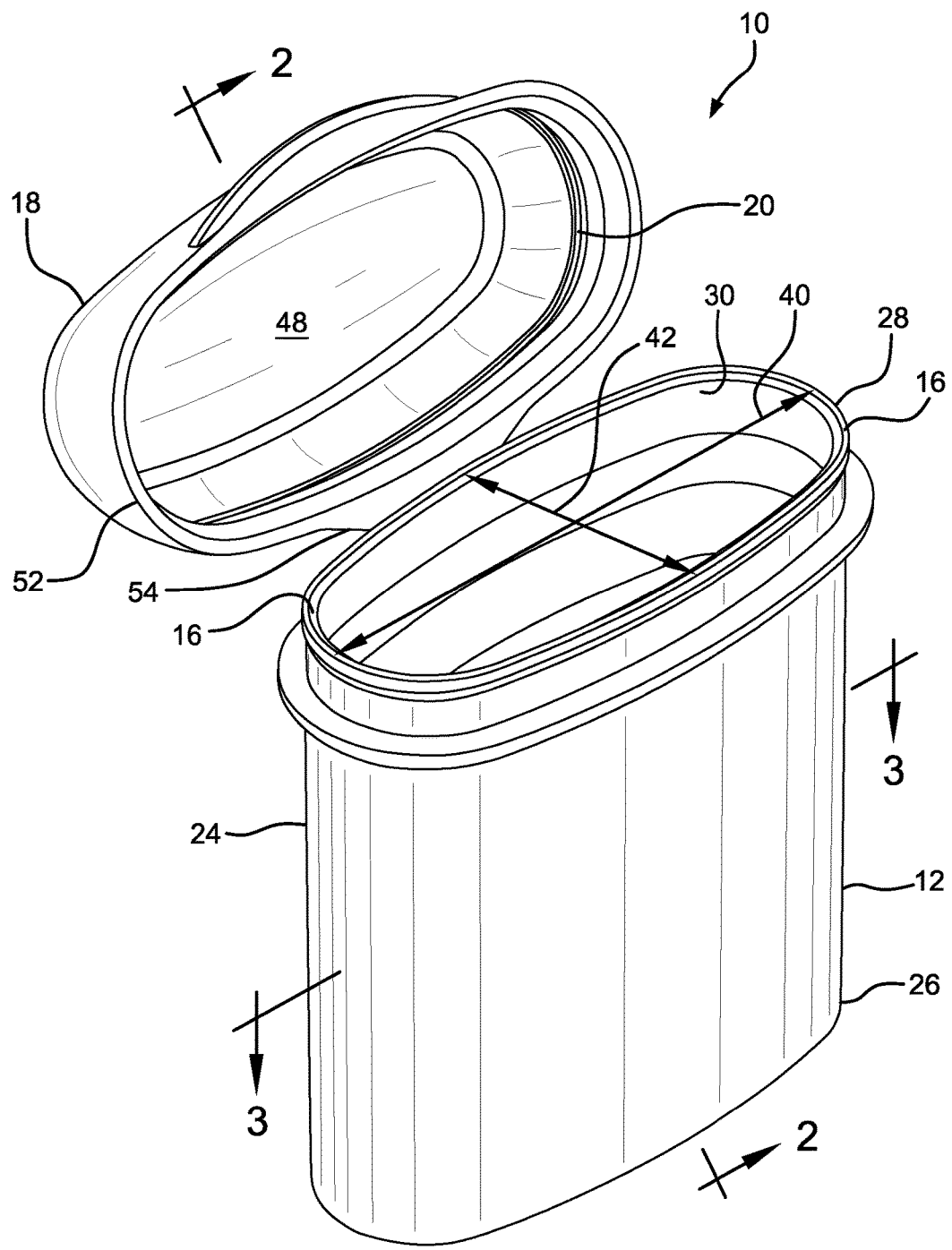
FIG. 1 is a perspective view of an embodiment of a container, shown with the lid open.

The following reference characters are used in the Figures.

| Ref. Char. | Description |
|---|---|
| 10 | Container |
| 12 | Body |
| 14 | Interior space |
| 16 | Body sealing surface |
| 18 | Lid |
| 20 | Lid sealing surface |
| 22 | Desiccant material |
| 24 | Generally tubular sidewall |
| 26 | First end (of 24) (base) |
| 28 | Second end (of 24) |
| 30 | Dispensing opening |
| 32 | Cross-section (of 24) |
| 34 | Major diameter (of 32) |
| 36 | Minor diameter (of 32) |
| 38 | Center (of 32) |
| 40 | Major diameter (of 16) |
| 42 | Minor diameter (of 16) |
| 44 | Body (FIG. 5) |
| 46 | Rounded corner (of 44) |
| 47 | Container (FIG. 6) |
| 48 | Closed surface (of 18) |
| 50 | Seal (of 16 and 20) |
| 52 | Skirt (of 18) |
| 54 | Integral hinge |
| 56 | Pivot axis (of 54) |
| 58 | Interior surface (of 24) |
| 60 | Interior portion of desiccant material |
| 62 | Interior portion (of 18) |
| 64 | Sachet |
| 66 | Canister |
| 68 | Pellet or particle |
| 78 | Inner seal |
| 80 | Container |
| 82 | Inner skirt |
| 84 | Seal gasket |
| 86 | Sealing surface |
| 88 | Contents |
| 90 | Lower end of 82 |
| 120 | Dispenser |
| 122 | Strip of material |
| 124 | Strip of material |
| 126 | Generally tubular body |
| 128 | Lid |
| 130 | Hinge |
| 132 | Long axis (of 126) |
| 134 | Short axis (of 126) |
| 136 | Sealing location (of 126) |
| 138 | Sealing location (of 128) |
| 140 | Interior surface |
| 142 | First end (of 126) (disposing opening) |
| 144 | Second end (of 126) |
| 146 | First platform |
| 148 | Integrally forward web |
| 150 | Second platform |
| 152 | Web |
| 154 | Reservoir |
| 156 | Region |
| 162 | Spline |
| 164 | Spline |
| 166 | Spline |
| 168 | Strip reservoir |
| 170 | Strip reservoir |
| 172 | Strip reservoir |
| 174 | Strip reservoir |
| 176 | Platform perforations through 150, 152 |
| 178 | Platform perforations through 150, 152 |
| 180 | Platform perforations through 150, 152 |
| 182 | Exterior shell (of 126) |
| 184 | Liner (of 126) |
| 186 | Lower end (of 184) |
| 188 | Interior surface (of 182) |
| 190 | Desiccant material (insert) |
| 192 | Desiccant material (in lid) |
| 194 | Perforation (in 150 and 152) |
| 196 | Desiccant sachet |
| 198 | Desiccant canister |
| 200 | Desiccant pellet |
| 202 | Embodiment (FIGS. 14 and 15) |
| 204 | Liner (FIGS. 14 and 15) |
| 206 | Insert (FIGS. 14 and 15) |
| 208 | Second platform (FIGS. 14 and 15) |
| 210 | Insert (FIG. 16) |
| 212 | Insert (FIG. 17) |
| 214 | Dispenser (FIG. 18) |
| 216 | Second platform (FIG. 18) |
| 218 | Portion (of 216) |
| 220 | Portion (of 216) |
| 222 | Compartment (FIG. 18) |
| 224 | Compartment (FIG. 18) |
| 226 | Second portion (of 216) |
| 228 | Second compartment (FIG. 18) |
| 230 | Top of 222 |
| 232 | Top of 228 |
| 234 | Floor (of FIG. 18) |
| 236 | Floor of (FIG. 18) |
| 240 | Third compartment (FIG. 18) |
| 250 | Top (of 124) (FIG. 12) |
| 252 | First cavity |
| 254 | End (of 256) |
| 256 | Core |
| 260 | Second cavity |
| 262 | End (of 264) |
| 264 | Core |
| 266 | Trimmed leading edge (of 256) |
| 268 | Face of 122 |
| 270 | Face of 124 |

DETAILED DESCRIPTION

U.S. Pat. Nos. 6,769,558 and 7,198,161 and European patent 1 220 794, all to the present inventor, disclose a leakproof, resealable, flip-top cylindrical container and cap assembly which comprises a cap and container attached by a hinge. A user is readily able to close the lid using the front tab on the lid. Those patents are incorporated here by reference for the characteristics and dimensions of a suitable seal for a container and cap assembly. When forming a moisture-tight seal using the flip-top closure described in the foregoing patents, the closure exerts a compressive force about the top of the container body. A sealing relationship is formed between the closure and the container body.

It is presently believed that the seal effectiveness, in large part, is due to the stiffness of the container walls. In an oval container (especially as the ratio between the major and minor axes becomes larger), the walls become less stiff against inward and outward deflection along the minor axis and are not able to withstand the force exerted by the closure. This lack of stiffness results in less seal integrity (i.e., a higher moisture ingress rate). In particular, the seal area of the sidewall of the container or cap is particularly subject to flexing along the minor axis, where the opposed walls have the largest radius in an oval container.

The present inventor has further determined that this problem can be addressed by providing a reinforcement stiffening the container against deflection along the minor axis. The reinforcement can be extra material in the container wall itself, but can also be provided, for example by press-fitting or otherwise incorporating an insert or liner into the container to reinforce its portions at or near the beginning and end of the minor axis. The insert, which also has utility to orient test strips, may be used to stiffen the sidewalls of the container.

Referring to FIGS. 1 through 4, a vial or container 10 is shown including a body 12, an interior space 14, a body sealing surface 16, a lid 18, a lid sealing surface 20, and a desiccant material 22 communicating with the interior space 14.

The body 12 can have a generally tubular sidewall 24 with first and second axially opposed ends 26 and 28 and a dispensing opening 30. The dispensing opening 30 is axially spaced from the first end or base 26 and at least adjacent to the second end 28. In the embodiment of FIGS. 1-4, at least a portion of the dispensing opening 30 is defined by the second end 28 of the sidewall 24.

The body 12 can have its interior space 14 disposed generally within the sidewall 24 and at least generally between the base 26 and the dispensing opening 30. The generally tubular sidewall 24 can have a cross-section 32, best shown in FIG. 3, having a major diameter 34 and a minor diameter 36 each passing through the center 38. The ratio between the major diameter 34 and the minor diameter 36 of the cross-section 32 can be, for example, a value between 1.1:1 and 10:1, inclusive. Alternatively, the ratio between the major diameter 34 and the minor diameter 36 of the cross-section 32 of the body sidewall 24 can be a value between 1.5:1 and 5:1, alternatively between 1.5:1 and 4:1, alternatively between 1.5:1 and 4:1, alternatively between 1.5:1 and 3:1, alternatively between 2:1 and 5:1, alternatively between 2:1 and 4:1, alternatively between 2:1 and 3:1, alternatively between 1.5:1 and 5:1, in each case the end points being inclusive. The upper and lower limits are not critical; the point of the ratios is to provide a container 10 that is wider than it is deep, or vice versa.

As illustrated in FIGS. 1-4, the body 12 is at least generally oval in cross-section 32. The body, however, can have other cross-sectional configurations. As illustrated in FIG. 5, the body 44 can be at least generally polygonal in cross-section, or at least generally rectangular in cross-section, and alternatively can have at least one rounded corner 46. Many other alternative configurations are also contemplated. For example, the container can be configured as shown in the container 47 of FIG. 1, with opposing concave and convex walls.

As illustrated in FIGS. 1-4, the body sealing surface 16 is not round, is located on the body 12, and is disposed about the dispensing opening 30. The body sealing surface 16 can have a major diameter 40 and a minor diameter 42, and the ratio between the major diameter 40 and the minor diameter 42 of the body sealing surface 16 can be a value between 1.1:1 and 10:1, inclusive. Alternatively, the ratio between the major diameter 40 and the minor diameter 42 of the body sealing surface 16 can be between 1.5:1 and 4:1, alternatively between 1.5:1 and 3:1, alternatively between 1.5:1 and 2:1, alternatively between 2:1 and 5:1, alternatively between 2:1 and 4:1, alternatively between 2:1 and 3:1, in each case the end points being inclusive. The upper and lower limits again are not critical, and provide a non-round sealing surface.

It should be understood that the ratio of the major and minor cross-section diameters 34 and 36 can be the same as or different from the ratio of the major and minor diameters 40 and 42 of the body sealing surface 16. Additionally, the shapes of the body sealing surface 16 and the cross-section 32 can be the same or different. For example, the cross-section 32 could be rectangular with rounded corners and the body sealing surface 16 could be elliptical. This is just one illustration of a possible alternative configuration.

The lid 18 comprises a closed surface 48 supporting the lid sealing surface 20. The lid 18 can be configured to seat on the body 12. It can have a lid sealing surface 20. The body sealing surface 16 and the lid sealing surface 20 can be configured to mate to form a seal 50 (best seen in FIG. 4) between the lid 18 and the body 12 when the lid 18 is seated on the body 12. When the seal 50 is formed, the lid 18 and the seal 50 defined by the sealing surfaces 16 and 20 at least substantially close the dispensing opening 30 and isolate the interior space 14 from ambient conditions.

Figure 4:
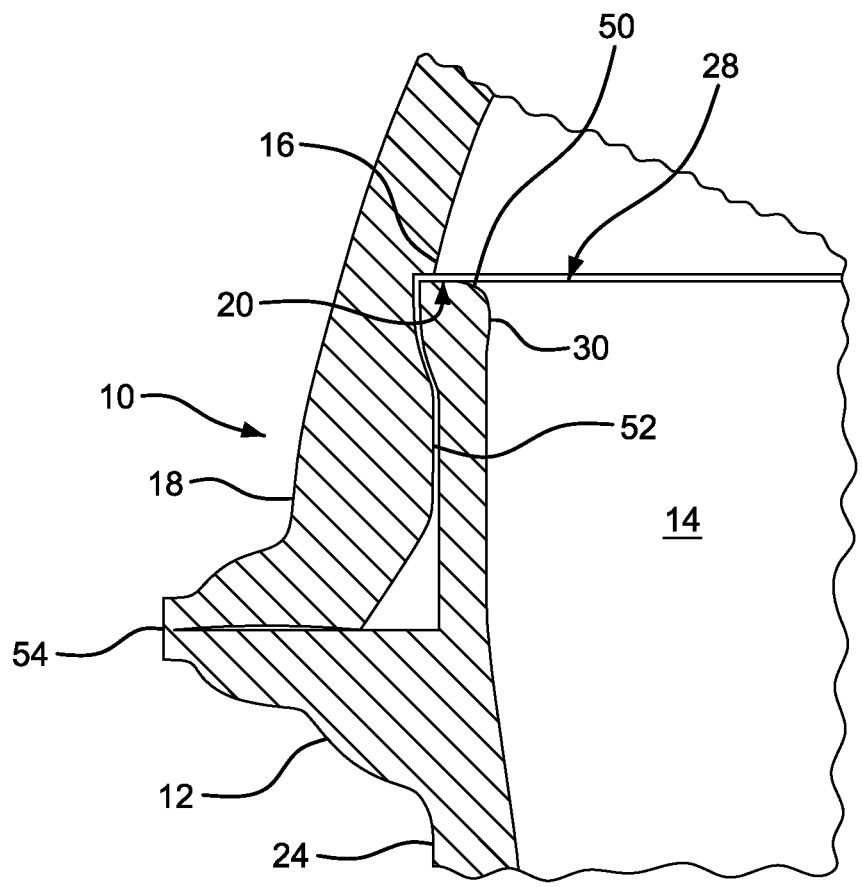
FIG. 4 is an enlarged detail view of the hinge and lid sealing surface shown in FIG. 2, modified to show the lid seated on the body.

The lid 18 of FIGS. 1-4 can have a generally tubular skirt 52 surrounding and depending from the lid sealing surface 20. The cross-section of the skirt 52 can be substantially congruent to the cross-section 32 of the body sidewall, at least substantially defining an extension of the generally tubular sidewall 24 when the lid 18 is seated on the body 12, as shown in FIG. 4.

In the illustrated embodiment of FIGS. 1-4, a tether, here configured as an integral hinge 54, links the body 12 and the lid 18. The hinge 54 can be configured to orient the lid 18 to seat on the body 12 when the lid 18 and body 12 are pivoted together. The illustrated integral hinge 54 of FIGS. 1-4, as illustrated, can extend from the sidewall 24 of the body 12 at least adjacent to the end of the minor axis 42. The integral hinge as illustrated defines a pivot axis 54 that can be generally parallel to the major diameter 40. In an alternative embodiment, the integral hinge could be displaced 90 degrees circumferentially and extend from the sidewall 24 of the body 12 at least adjacent to the end of the major diameter 40. The integral hinge could then define a pivot axis that could be generally perpendicular to the major axis 40. The integral hinge could also be displaced to an intermediate point between the ends of the major diameter 40 and minor diameter 42, in another alternative embodiment, providing an oblique pivot axis parallel neither to the major diameter 40 nor the minor diameter 42.

The inventors have found that a non-round seal, for example the seal 50 shown in FIGS. 1-4 formed by mating the non-round body sealing surface 16 and lid sealing surface 20, does not exclude moisture as well as a round seal. Nonetheless, it may be necessary or useful to limit the amount of moisture entering or leaving the interior space 14 of the container 10, as when the contents of the container 10 are moisture-sensitive. The inventors have found that the issue of moisture sensitivity caused by a non-round seal can be addressed and at least partially alleviated if the container 10 includes a desiccant material such as 22 communicating with the interior space 14 of the container 10 when the lid 18 is seated on the body 12.

An example of suitable desiccant material 22 is the injection-moldable thermoplastic desiccant polymeric material described in one or more of U.S. Pat. Nos. 5,911,937; 6,214,255; 6,130,263; 6,080,350; 6,174,952; 6,124,006; and 6,221,446, all to Hekal. These patents are incorporated here by reference. Silica gel, a molecular sieve, calcium oxides or clay may also or instead be used directly as desiccants or incorporated into a desiccant material. The desiccant alternatively can be a material adapted to release a gas, such as an inert gas that prevents oxidation of the enclosed medicament, a flavoring or fragrance, or moisture, in the case of a medicament that should not be allowed to dry out.

For example, in the container 10 of FIGS. 1-4, the interior space 14 can be defined at least in part by an interior surface 58 of the body 12 made of a desiccant material 22. In the container 10 of FIGS. 1-4, at least one of the ends of the container 10, here the first end 26, also can have an interior portion 60 made of desiccant material. Additionally or alternatively, the lid 18 can have an interior portion 48 that can be integrally molded of desiccant material 22. Additionally or alternatively, the interior surface 58 of desiccant 22 can be defined by a separately molded sleeve of desiccant material 22 placed within the body 12 and at least partially defining the interior space 14. The sleeve can be integrally formed with at least one of the sidewall and an end wall.

Figure 2:
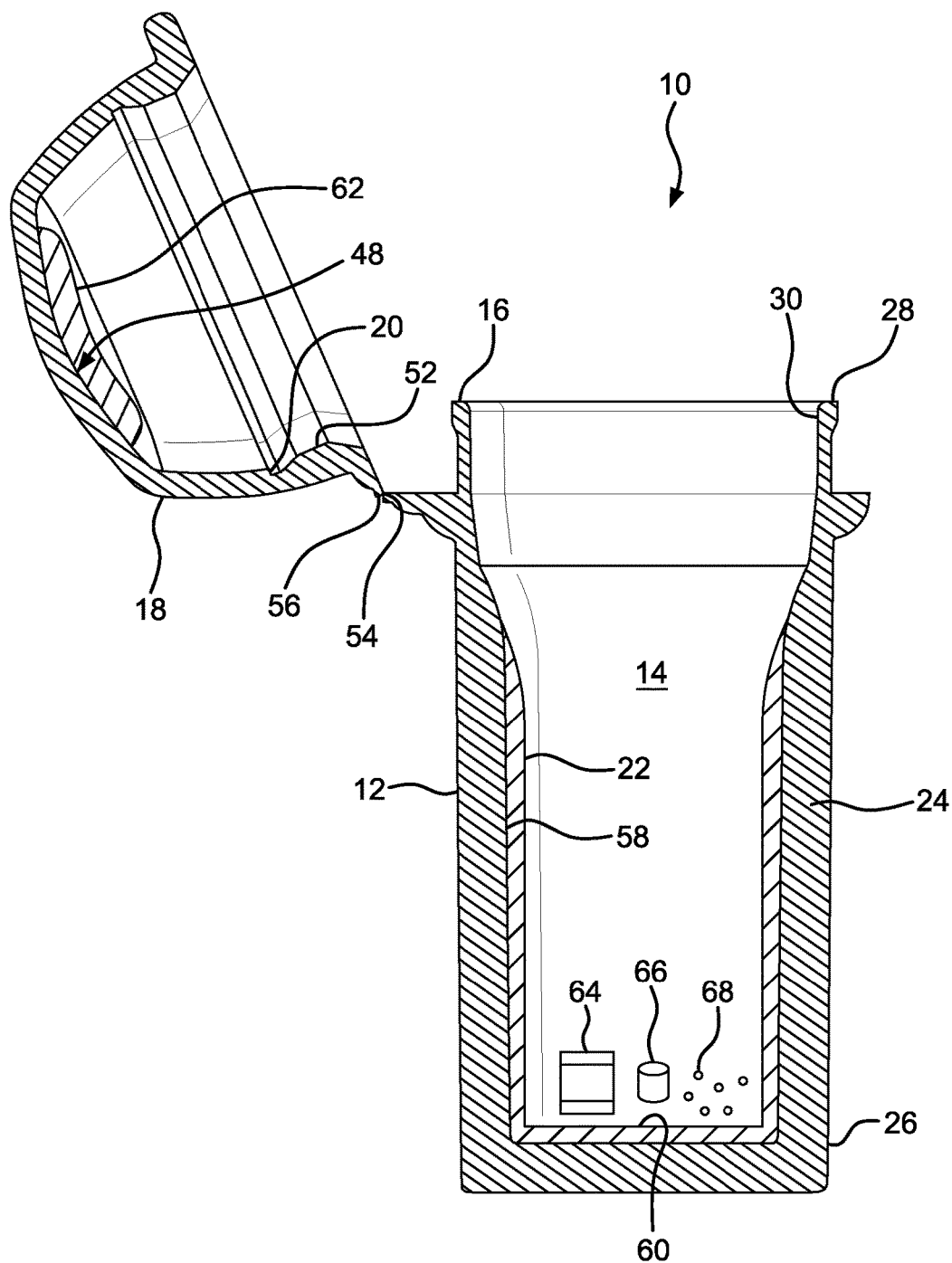
FIG. 2 is a longitudinal section taken along section line 2-2 of FIG. 1.

In an alternative or additional embodiment, also illustrated in FIG. 2, at least a portion of the desiccant material 22 can located in the interior space 14. For example, as shown in FIG. 2, at least a portion of the desiccant 22 can be provided in the form of one or more sachets 64, or canisters 66, or a particulate material 68, which can be provided as pellets or in other particulate forms.

Figure 7:
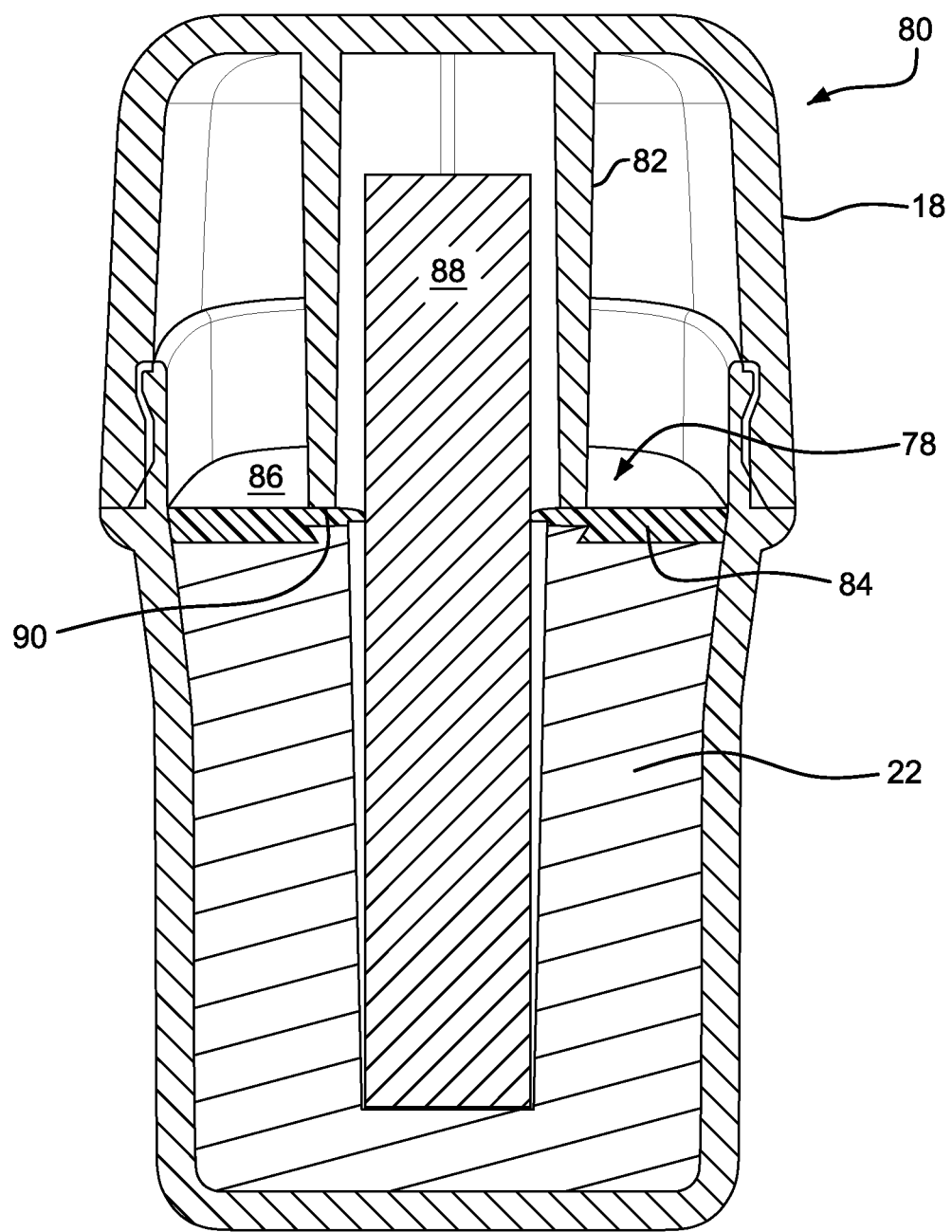
FIG. 7 is a cross-section of an additional embodiment of the invention.

Referring now to FIG. 7, a secondary seal generally indicated at 78 is disclosed for a container 80 otherwise similar to that of FIGS. 1-4. In FIG. 7, the lid 18 has an inner skirt 82 and the body 12 contains a desiccant insert 22 and a generally annular seal gasket 84 having a sealing surface 86 encircling the contents 88 of the container. The inner skirt 82 has a distal or lower end 90 bearing against the seal gasket 84, forming the seal. The seal gasket 84 can be made of an elastomeric material (for example a thermoplastic elastomer, TPE.) One contemplated TPE is Santoprene®, which is a registered trademark of Monsanto Company of St. Louis, Mo., U.S.A.

The position of the lower end 90 of the web 82, and thus the seal 78, can be closer to the outer skirt 52 of the lid than illustrated in FIG. 7, which may be useful to allow more space within the inner seal 80. The gasket 86 can alternatively be reduced to just the portion beneath the lower end 90 of the inner skirt 82, although an advantage of the illustrated embodiment is that the material of the seal gasket 84 can also isolate the top surface of the desiccant material 22 from direct contact with the environment when the container 80 is opened.

In any embodiment an elastomer may also be located along the top interior surface of the vial body 12, such as the body sealing surface 16, to resiliently seat against the lid sealing surface 20.

A secondary sealing element can also or alternatively be formed along the inside surface of the flip-top lid 18. The secondary sealing element may be located in close proximity to the sidewall or skirt 52 of the flip-top lid 18. When the lid 18 is closed, the secondary sealing element compresses the elastomer along the top surface of the insert to form a secondary seal, in combination with the seal according to U.S. Pat. No. 6,769,558 and other patents as previously described.

More generally, any one or more of the desiccant or sealing features shown in the Figures can be used individually or together, and additional embodiments deploying the desiccant or sealing elements in other ways are also contemplated.

The container 10 can be made in various ways. In one embodiment, the container 10 and its desiccant feature 22 can each be separately injection molded from thermoplastic material, as in a one-shot or two-shot injection process, then assembled. The first mold is used to produce the flip-top vial 10 or 80. In second mold, an insert is molded. The lid 18 and integral hinge 54 can be integrally formed in the same mold as the outer body 12. In one embodiment, the flip-top vial lid is closed in the mold.

Alternatively, the body 12 and the desiccant polymeric material 22 can formed in two shots in one injection mold.

In the embodiment of FIG. 7, the insert is composed of two materials: a desiccant plastic 22 and an elastomeric material 84. The insert 22 and seal gasket 84 may be molded in a 2-shot injection molding process. The desiccant material 22 of the insert is formed in the first shot. Next, the elastomeric material 84 is formed in the second shot. The composite insert is assembled into the vial. Alternatively, the seal material and the material of the body 12 or lid 18 can be formed in a single, two-shot mold.

One of many known examples of suitable material for the outer portions of the container 10 can be polypropylene—a moisture blocking polymeric material. For example, the outer body 12 and lid 18 can be made of polypropylene, and the desiccant features such the interior portion 60 can be made of a desiccant material.

The container can also be made as disclosed in any of the embodiments of U.S. Ser. Nos. 61/053,277 or 29/318,272, which are incorporated by reference above.

When the insert is assembled into the vial, the elastomeric material 84 forms a secondary seal along the top interior surface of the vial flip-top lid.

Figure 8:
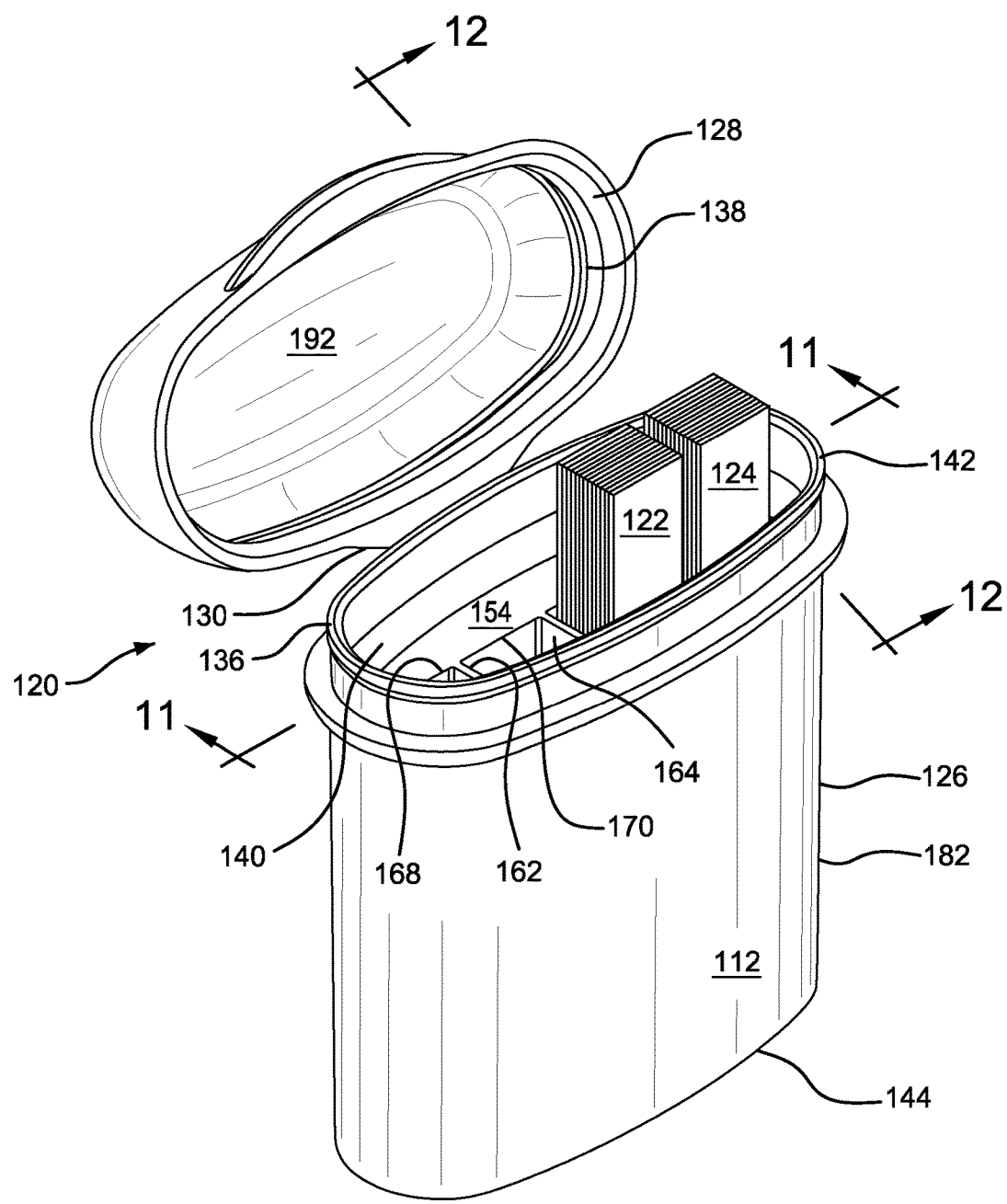
FIG. 8 is a perspective view of an embodiment of the dispenser.
Figure 9:
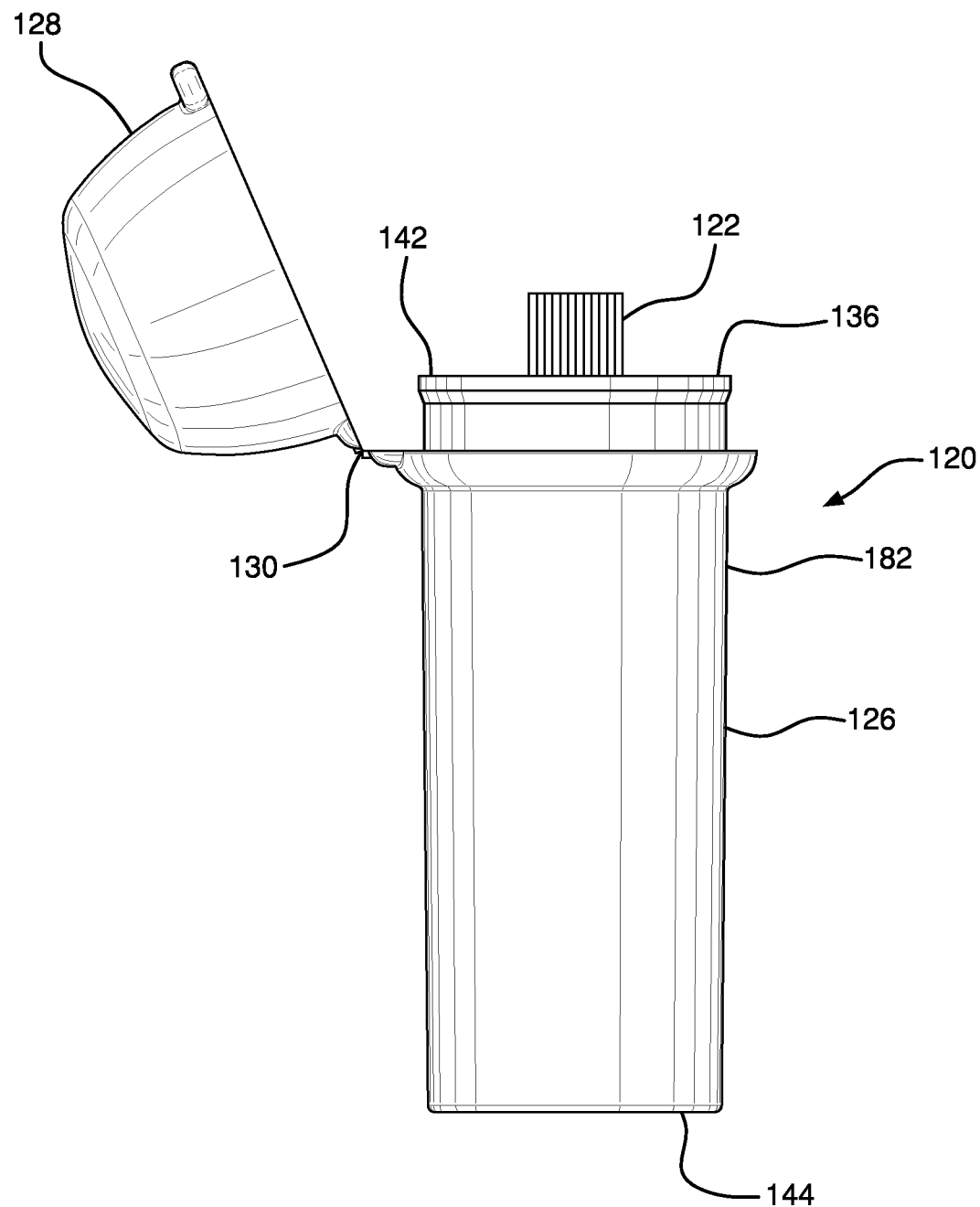
FIG. 9 is a side elevation of the embodiment of FIG. 8.
Figure 10:
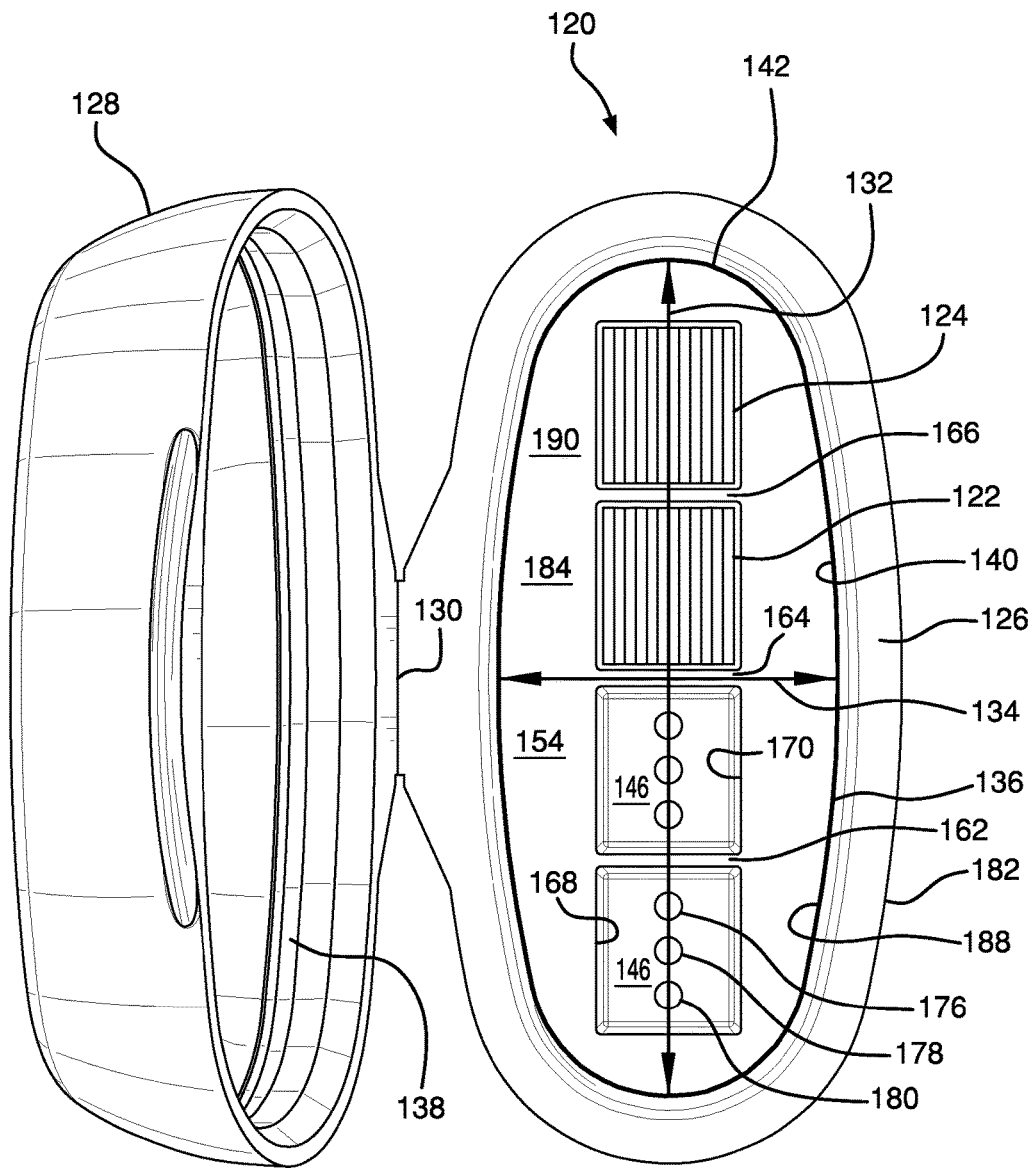
FIG. 10 is a plan view of the embodiment of FIG. 8.

Referring more particularly to FIGS. 8-10, the illustrated dispenser 120 is a vial including a generally tubular body 126 and a lid 128 joined together by a hinge 130. In this embodiment the body 126 is generally oval or elliptical in cross-section, having a laterally extending long axis 132 (running from top to bottom in FIG. 10) and a laterally extending short axis 134 (running from side to side in FIG. 10). Optionally, the body 126, lid 128, and hinge 130 can be integrally formed, as by molding the assembly in a one-shot injection mold to form the body 126, the lid 128, and an integral hinge 130 simultaneously. The body 126, lid 128, and hinge 130 can be made of any suitable material, commonly a substantially moisture-impervious material and commonly a thermoplastic material that is useful for injection molding. The body 126, lid 128, and the hinge 130 can be made of polypropylene or polyethylene, for example, to provide good moisture protection.

The lid 128 and body 126 respectively have first and second sealing locations 36 and 38 which are mateable when the lid 128 is seated on the body 126 to at least substantially seal the dispensing opening 142 and minimize contact of water vapor or other environmental substances with the test strips such as 122 and 124 or other contents of the dispenser 120. The body 126 has an interior surface 140 and first and second axially opposed ends 142 and 144, and at least one of the ends, here the end 142, defines a dispensing opening.

Figure 11:
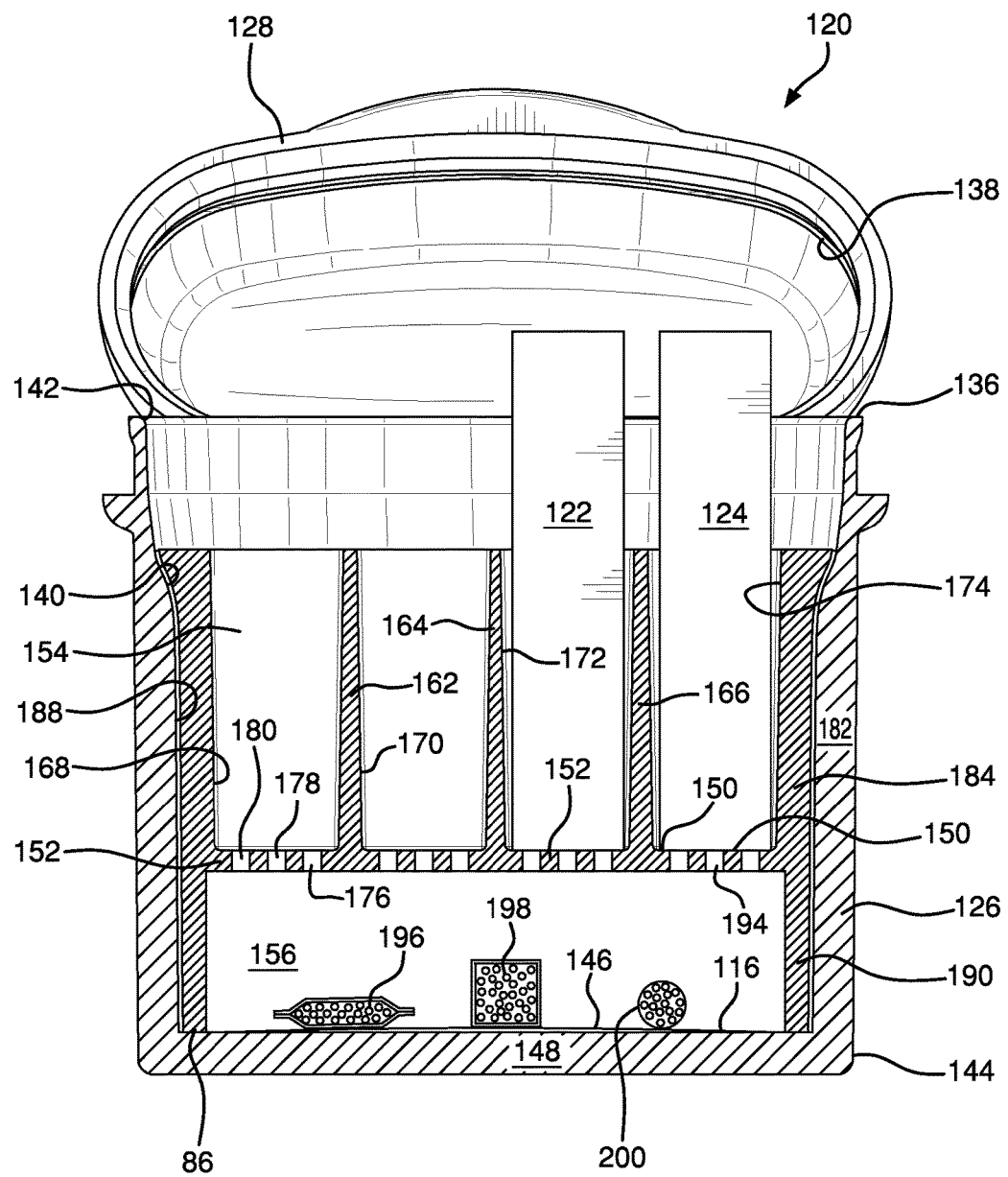
FIG. 11 is a section of the embodiment of FIG. 8 taken along section lines 11-11.
Figure 12:
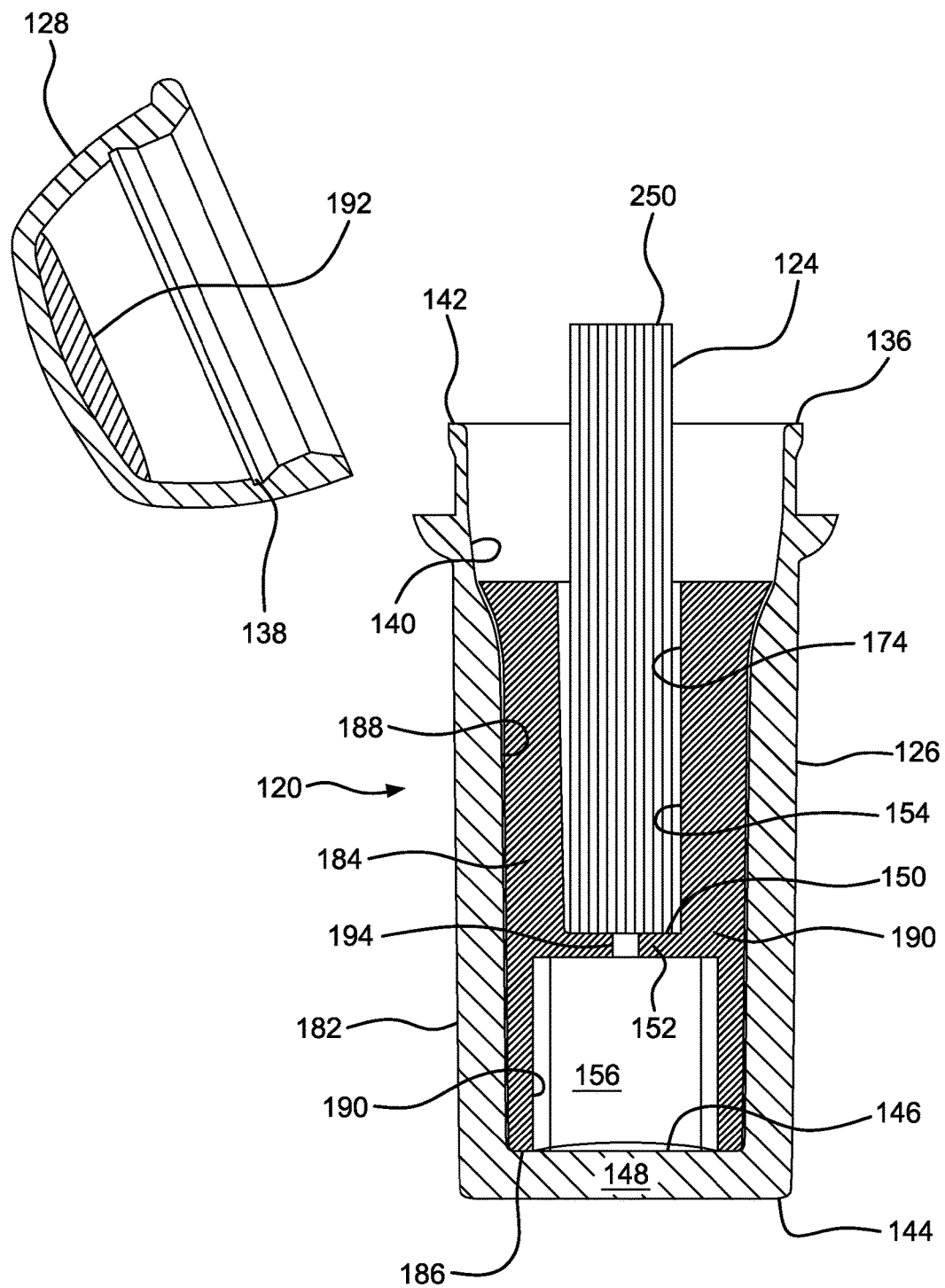
FIG. 12 is a section of the embodiment of FIG. 8 taken along section lines 12-12.

FIGS. 10-12 in particular show various interior details of the embodiment of FIG. 8.

The body 126 has a first platform 146, in this embodiment defined by the upper surface of an integrally formed web 148. (Words of orientation such as "upper," "lower" or "lateral" in this specification refer to the dispenser 120 when it is oriented as shown in FIGS. 11-12. "Axial" is up or down as shown in FIGS. 11 and 12, and "lateral" refers to any direction having a component perpendicular to axial For example, a direction perpendicular to axial and a direction forming an angle of 45 degrees with respect to axial are both lateral directions.) The first platform 146 extends laterally within the interior surface 140 and is positioned at least substantially at the end 44 of the body.

The body 126 has a second platform 150 extending laterally within the interior surface 140. The second platform 150 is positioned between and spaced axially from the first platform 146 and the dispensing opening 142. In the embodiment of FIGS. 8-12, the second platform 150 is defined by the upper surface of a laterally extending web 152.

The second platform 150 is positioned and configured to provide adequate elevation to extend the test strips 122, 124 beyond the top lip or dispensing opening 142 of the vial body 126 and position them within the lid 128 (when closed) without damaging the exposed ends of the test strips. Damage could occur when the lid is closed and strips such as 122, 124 lean or bend over and get trapped between the vial body 126 and the lid 128.

By extending the test strips 122, 124 beyond the dispensing opening 142 of the vial body, the end user will have substantially easier access to the test strips 122, 124 presented to the user when the vial lid 128 is open. Since commercial test strips have many different lengths, the second platform 150 of the dispenser 120 can be easily adjusted to the test strip length to consistently be able to provide a package that presents the test strips to the consumer uniformly, regardless of the test strip length, without necessarily changing the overall length of the generally tubular body 126.

Additionally, the first and second platforms 146 and 150 can provide a method to increase the amount of desiccant being used for enhanced shelf life protection. It is more difficult to obtain a moisture tight seal on the illustrated oval dispenser 120 than on a round dispenser. The platforms allow additional desiccant to be added to the dispenser 120 for enhanced shelf life protection. Oval vials also are more difficult to manufacture due to the difference in shrinkage of the primarily flat sides as opposed to the sharper corners on the ends. This non-uniform geometry causes differences in shrinkage rates compared to a round vial.

Figure 19:
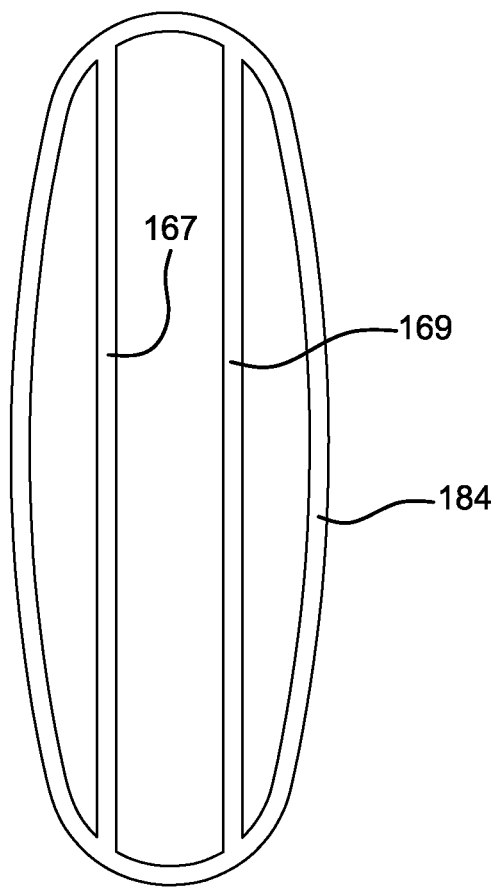
FIG. 19 is a fragmentary plan view of an alternative embodiment in which the splines run perpendicular to their orientation shown in FIG. 10.

A reservoir generally indicated at 154 is located between the second platform 150 and the dispensing opening 142, and a region generally indicated at 156 is located between the first and second platforms 146 and 150. At least one spline or partition 162, and in the embodiment of FIGS. 8-12 three parallel splines 162, 164, and 166, extend axially and laterally within the reservoir 154 and subdivide the reservoir into plural axially extending compartments or strip reservoirs, such as 168, 170, 172, and 174, communicating with the dispensing opening 142. In this embodiment, the splines 162, 164, and 166 lie substantially parallel to the laterally extending short axis 134 of the oval. In an alternative embodiment, as illustrated in FIG. 19, the splines such as 167 and 169 could lie substantially parallel to the laterally extending long axis 132 of the oval.

Partitioning the reservoir 154 using splines 162, 164, and 166 allows discrete placement of the test strips 122, 124, keeping them neatly arranged and more compact than random placement. Additionally the splines 162, 164, and 166 assist in maintaining the test strips upright for presentation to the customer. Together with the body 126 and insert 190, the splines 162, 164, and 166 position the test strips 122, 124 away from the sealing locations 136 and 138 to prevent the test strips 122, 124 from being lodged between the sealing locations 136 and 138 while closing the lid 128.

The dispenser 120 can have an open path of communication, such as the platform perforations 176, 178, and 180 in the second platform 150 and web 152, between the reservoir 154 and at least one of the strip reservoirs, such as 168. In the embodiment of FIGS. 8-12, an open path of communication is provided between the reservoir 154 and each of the strip reservoirs 168, 170, 172, and 174.

In the dispenser, the body 126 and at least one of the first platform 146, the second platform 150, and a spline such as 162, 164, 166, and 168 are integral. In the dispenser of FIGS. 8-12, for example, the body and the first platform are integral.

In the embodiment of FIGS. 8-12, with particular reference to FIGS. 11 and 12, the body 126 includes an exterior shell 182, which can be made of moisture-impervious material integrally formed with the first platform 146 and web 148. In the dispenser of FIGS. 8-12, at least a portion of the body and at least a portion of the first platform are formed in one shot in an injection mold, forming a first part.

A generally tubular liner 184 is provided, here including the second platform 150 and the splines 162, 164, and 166. At least a portion of the second platform 150 and the splines 162, 164, and 166 are formed in a single shot in an injection mold, forming a second part. The first and second parts are assembled to provide a dispenser 120.

The liner 184 of the embodiment shown in FIGS. 8-12 has a lower end 186 that, in the illustrated embodiment, abuts the first platform 146 to locate the liner 184 precisely within the body 126. The axial distance between the second platform 150 and the dispensing opening 142 can be selected by providing a lower end 186 that is spaced a corresponding distance from the second platform 150. This allows the dispenser 120 to be customized for strips 122 of a particular length without changing the mold used to form the exterior shell 182.

By providing an assembly of a separately molded liner 184 and shell 182, each of these parts can be made, in whole or in part, in a one-shot injection mold, without the need for side draws or other complicated and expensive molding or machining techniques that would otherwise be needed to make such an extensively undercut part. In the embodiment of FIGS. 8-12, the body 126 and each of the first platform 146, the second platform 150, and the splines 162, 164, 166, and 168 are injection molded, although that is not an essential feature.

A desiccant optionally can be incorporated into the dispenser 120 to keep the partial pressure of water vapor within the dispenser 120 relatively low compared to ambient conditions. One objective can be to reduce the partial pressure of water vapor in the reservoir 154 where the strips such as 122 and 124 are stored. A desiccant can be provided anywhere within the enclosure formed by the exterior shell 182, including but not limited to on an interior surface 188 of the shell 182 itself.

For example, the shell 182 could be partially or entirely molded from an injection moldable desiccant composition. Suitable desiccant plastics include, but are not limited to, those disclosed in U.S. Pat. Nos. 5,911,937; 6,214,255; 6,130,263; 6,080,350; 6,174,952; 6,124,006; and 6,221,446, all to Hekal. These disclosures of these patents are incorporated herein by reference. Silica gel, a molecular sieve, calcium oxides or clay may be used directly as desiccants or incorporated into a desiccant material. The desiccant can also or instead be a material adapted to release a gas, such as an inert gas that prevents oxidation of the enclosed medicament, a flavoring or fragrance, or moisture, in the case of a medicament that should not be allowed to dry out.

The reservoir 154 can be desiccated, for example, by providing a desiccant material such as 190 that is exposed to the reservoir 154. "Exposed" as used here is a broad term including direct contact between the desiccant and the reservoir to be desiccated, as well as communication between the desiccant 190 and the reservoir 154, optionally via a passage or series of passages lying between the desiccant such as 190 and the reservoir 154.

For example, with reference to FIG. 12, a desiccant material 192 provided in the lid 128 is exposed to the desiccant region 156. A desiccant material 190 is also exposed to the reservoir 154, in this instance via the region 156 and the platform perforation 194. The platform perforation 194 communicates between the region 156 and the reservoir 154. With reference to FIG. 11, the desiccant packet or sachet 196, the desiccant canister 198, and the desiccant pellet 200 are also each exposed to the reservoir 154.

FIG. 11 also illustrates a dispenser 120 in which the desiccant materials 190, 196, 198, and 200 are each in contact with the region 156. As used here, "contact" has a more specific definition that requires the desiccant to be within or adjacent to the region 156.

The dispenser can have at least a portion of any one of the body interior surface 188, a spline such as 162, 164, or 166, the first platform 146, or the second platform 156, or any combination of these parts, composed of a desiccant material.

The dispenser 120 can also include a desiccant such as one or more sachets 196, canisters 198, or pellets 200 disposed in the region 156. "Disposed in" is a more particular term meaning that the desiccant is located within the boundaries of the region 156. One advantage of the embodiment of FIGS. 8-12 is that it provides a considerable amount of space in the region 156 to place one or more sachets such as 196 or canisters such as 198 containing particulate material, or free pellets or particulate material such as 200 containing or made of desiccant material. The region 156 thus can provide a desiccant reservoir at least somewhat isolated from the reservoir 154. In an embodiment, the region 156 can be sized to contain a suitable amount of desiccant of any type or form to maintain a low water vapor pressure in the reservoir 154.

The sleeve 184 of desiccant material disposed within the body 126 can at least partially define at least one of the reservoir 154 and the region 156. In the embodiment of FIGS. 8-12, the sleeve partially defines each of the reservoir 154 and the region 156.

Figure 13:
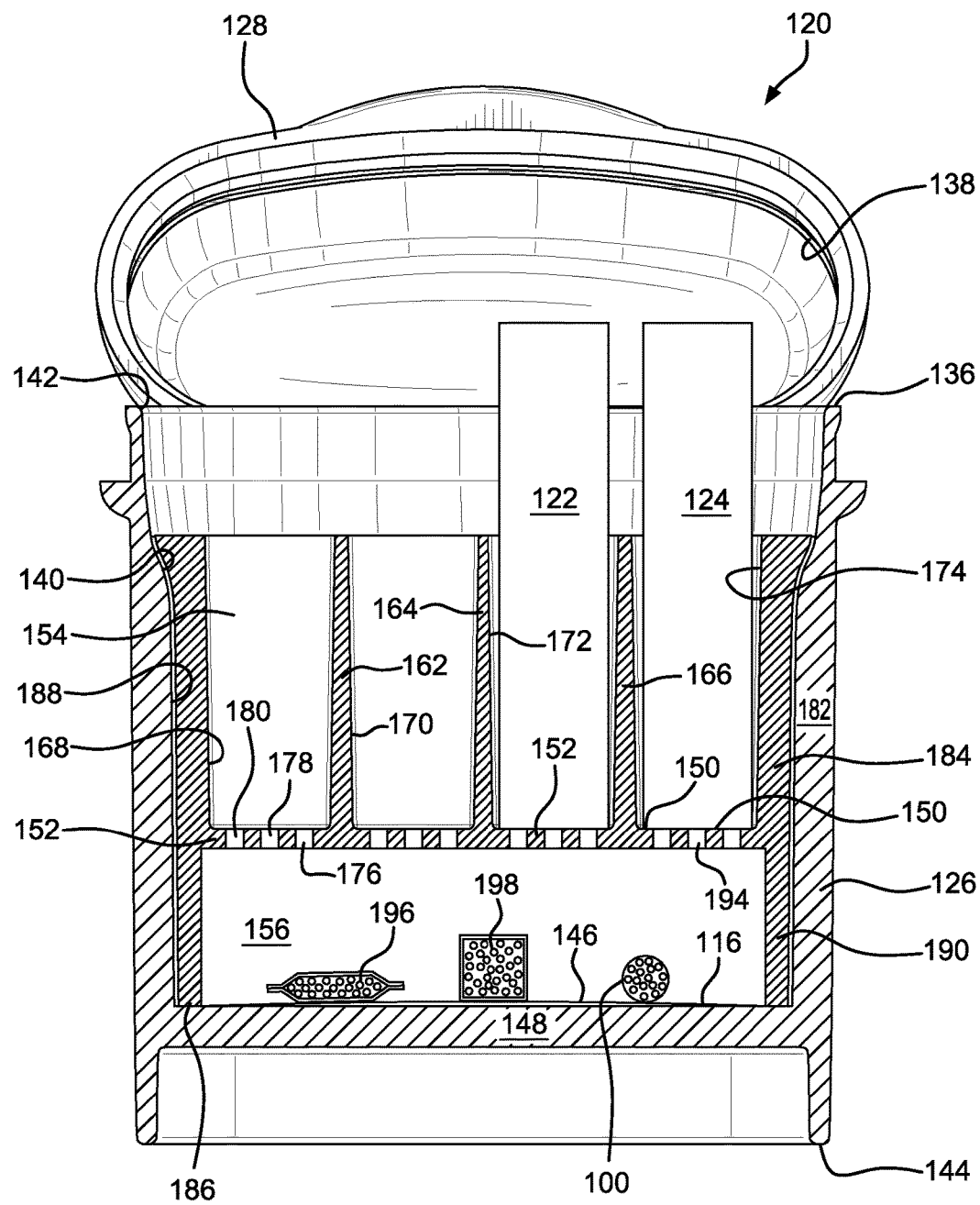
FIG. 13 is a modification of FIG. 11, showing as an alternative a false bottom defined by the web 148 recessed in the body 126.

FIG. 13 shows an alternative embodiment, compared to FIG. 11, in which the dispenser 120 has a false bottom defined by the web 148. In this embodiment, the first platform 146 is located between the axially opposed ends 142 and 144 of the body. In this embodiment, the first platform 150 can be positioned between the ends 142 and 144 to provide adequate elevation to extend the test strips 122, 124 beyond the top lip or dispensing opening 142 of the vial body 126 and position them within the lid 128 (when closed) without damaging the exposed ends of the test strips. The position of the first platform 146 thus can be adjusted along with or independently of the position of the second platform 150 to adjust the positions of the tops of the test strips such as 122 and 124 in the container 120.

Figure 14:
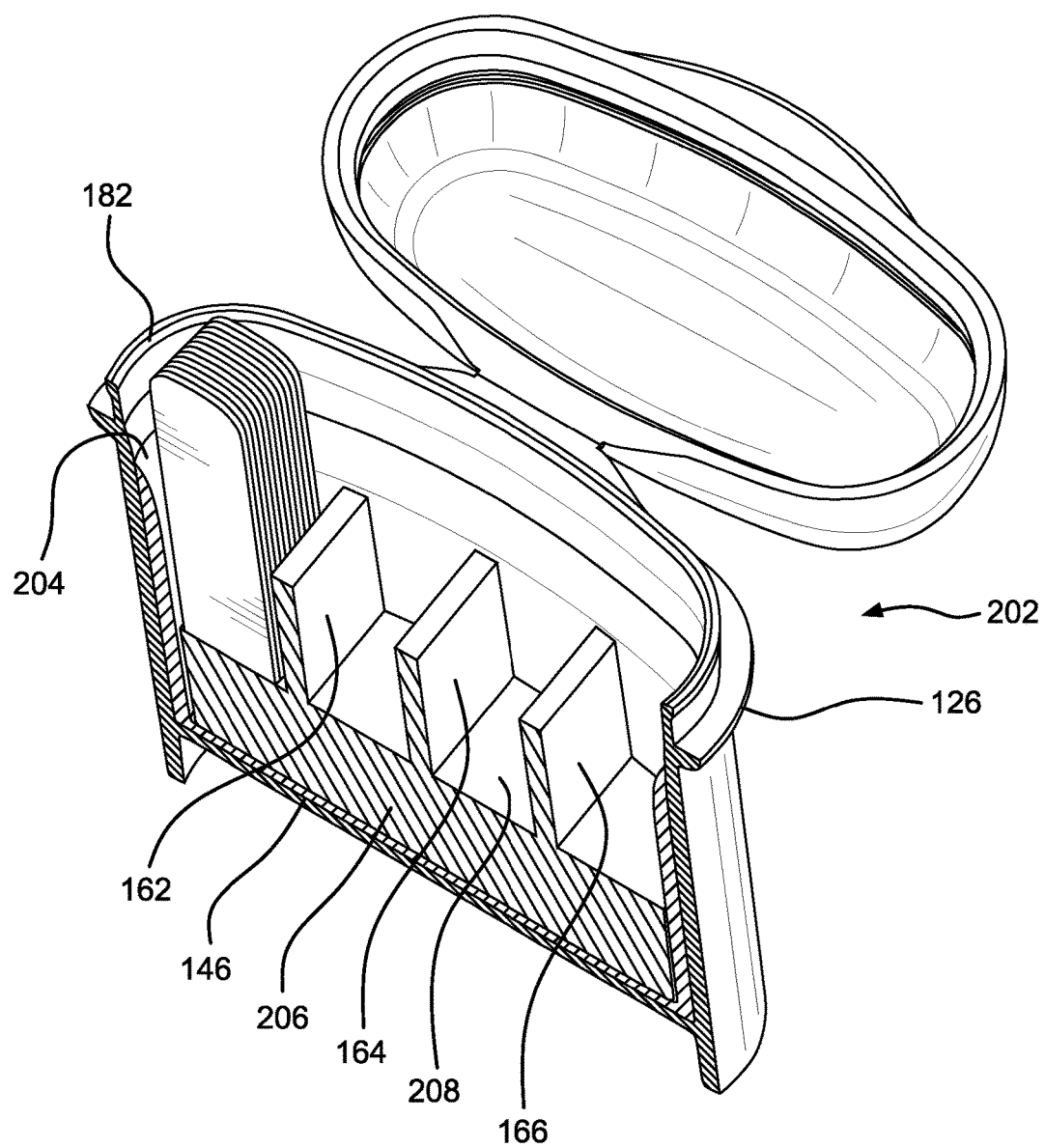
FIG. 14 is a cutaway perspective view of another embodiment of the invention.
Figure 15:
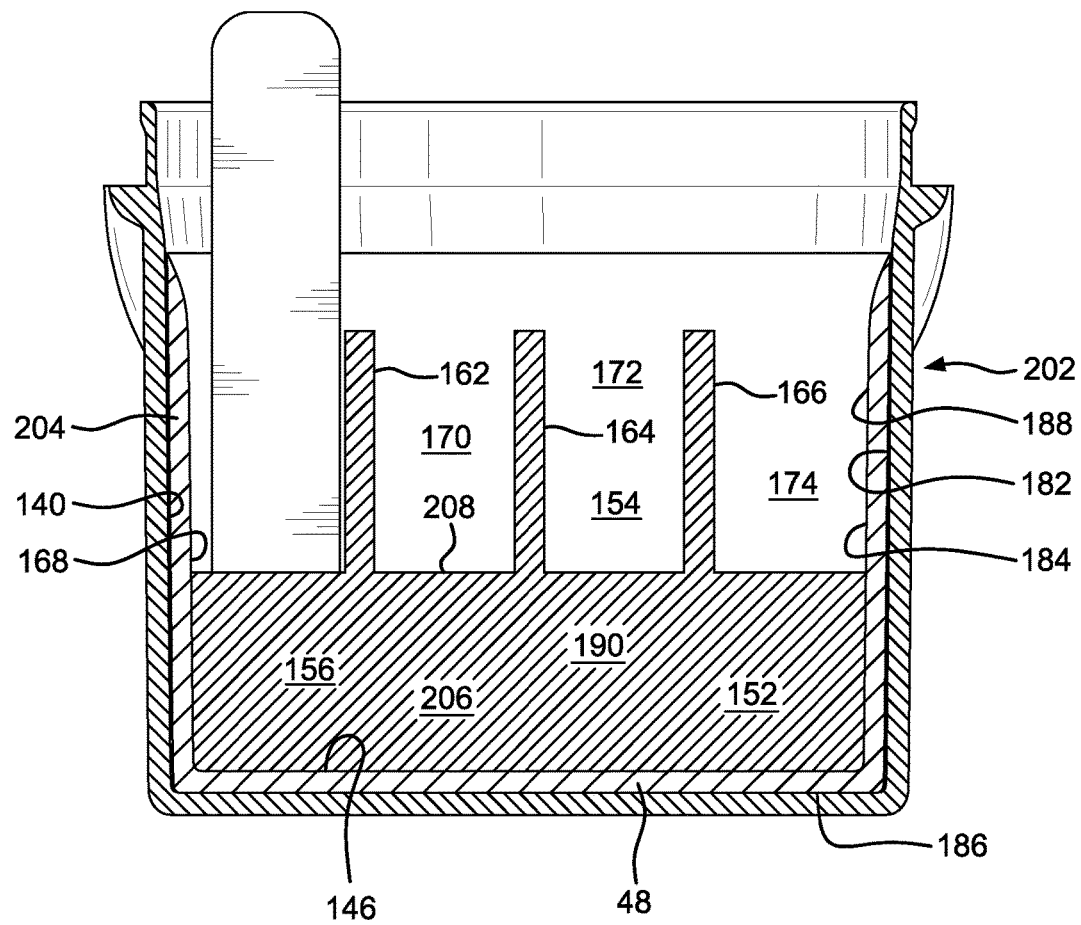
FIG. 15 is a sectional view of the embodiment of FIG. 14.

FIGS. 14 and 15 show an alternative embodiment 202 in which an internal side wall or liner 204 of desiccant material is formed within the exterior shell 182 and web 152 of the body 126 in a two-shot injection molding process. The construction material can be desiccant plastic, a traditional three phase polymer or a two phase polymer, for example. The liner may also be molded from a non-desiccated polymer such as polyethylene, polypropylene or other suitable materials.

The thickness and height of the liner 204 can be adjusted to provide tailored moisture protection to the vial or tailor the internal volume. The liner 204 also provides stiffness to the vial which facilitates a moisture tight flip-top seal. By increasing or reducing the thickness or height of the liner walls, the sidewall deflection is adjusted to facilitate closure of the lid onto the vial body.

In this embodiment, the first platform 146 is defined by desiccant material integral with the interior surface 140. An insert 206 made of desiccant material is also provided. The insert 206 defines the second platform 208 and the splines 162, 164, and 166, and substantially fills the entire region 156 of the dispenser as well as the portion of the reservoir 154 occupied by the splines 162, 164, and 166.

Figure 16:
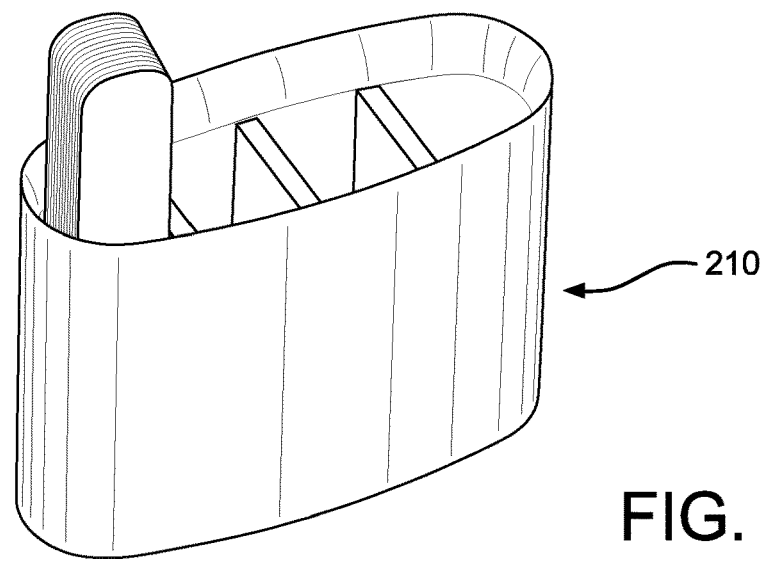
FIG. 16 is a perspective view of a desiccant insert defining another embodiment of the dispenser.
Figure 17:
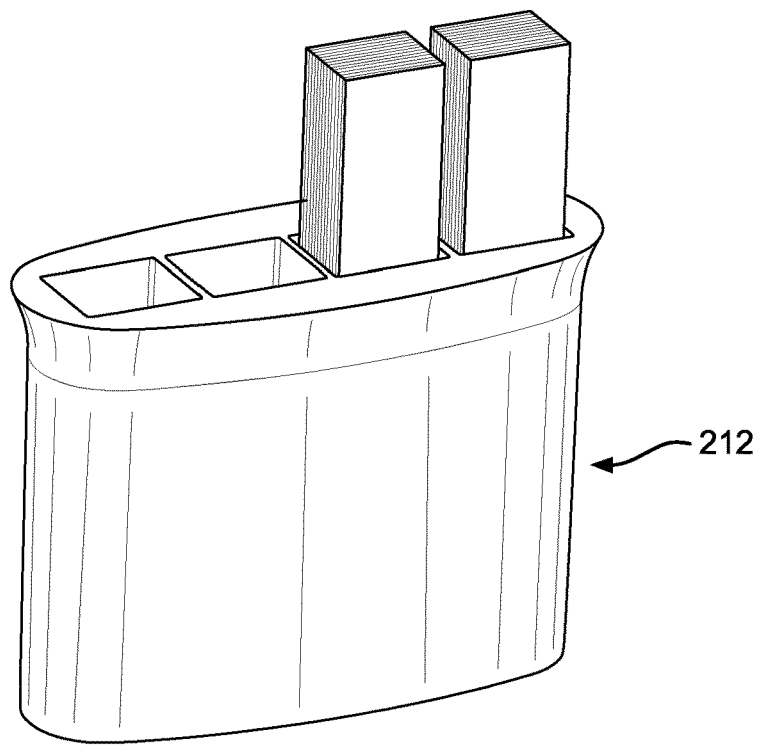
FIG. 17 is a perspective view of another desiccant insert defining still another embodiment of the dispenser.

FIGS. 16 and 17 show alternative embodiments of inserts, respectively 210 and 212.

Figure 18:
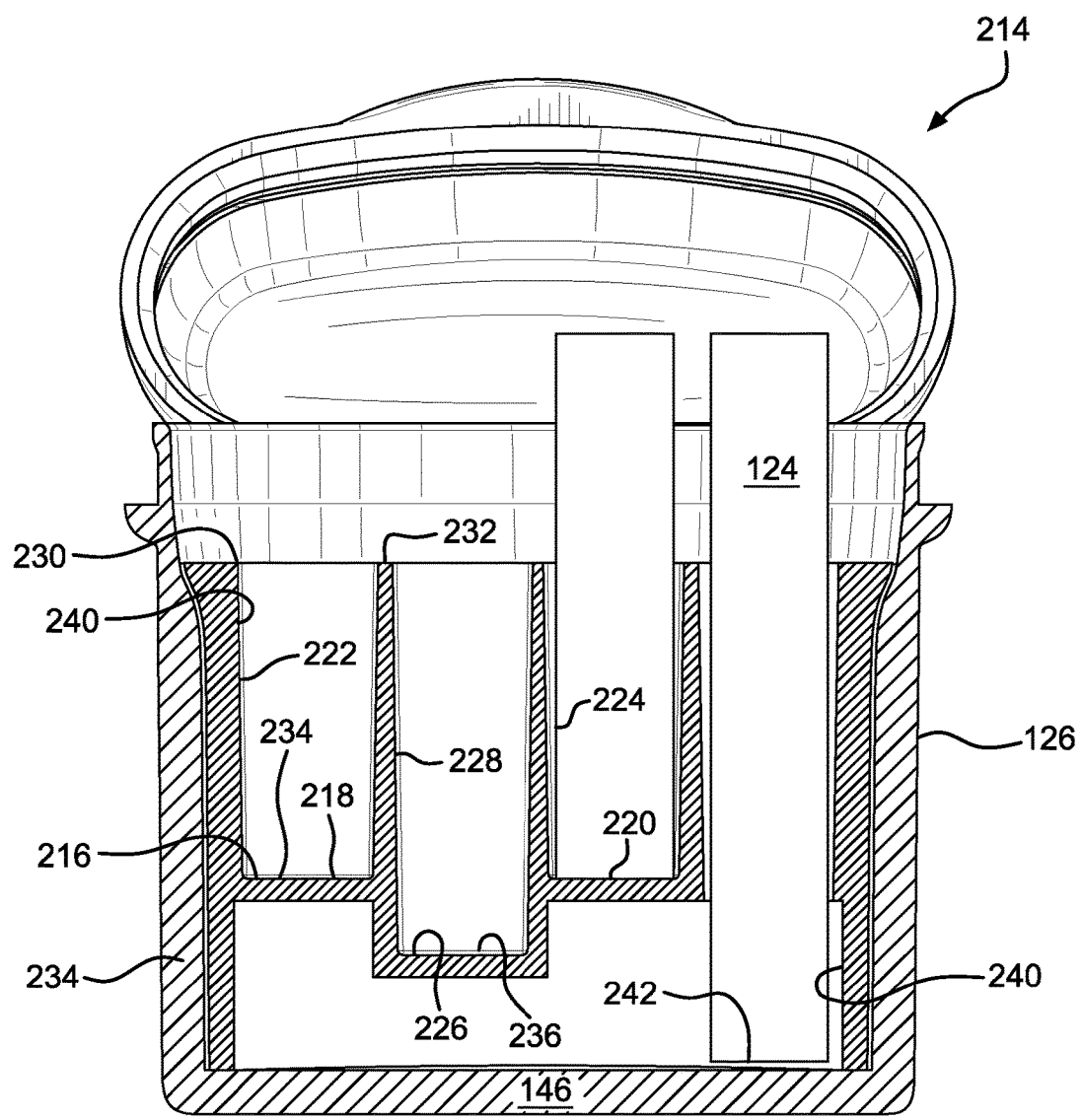
FIG. 18 is a view similar to FIG. 15 showing other potential modifications to accommodate and uniformly present strips having different lengths.

FIG. 18 shows an alternative embodiment of a dispenser 214 in which the second platform 216 has a first portion 218 or 220 defining a first strip reservoir (respectively 222 or 224) and a second portion 226 non-coplanar with the first portion 218 or 220 and defining a second strip reservoir 228. The strip reservoirs 222 and 228 have tops, respectively 230 and 232, at the same elevation and floors, respectively 234 and 236, at different elevations, so the second strip reservoir 228 is axially longer than the first strip reservoir 222.

Also in FIG. 18, a strip reservoir 240 is located beside the second platform 216, and extends down to and is defined by a portion 242 of the first platform 146. The strip reservoir 240 is axially longer than the strip reservoirs 222, 224, and 228, and thus can accommodate even much longer strips 124 than the others.

One optional advantage of the illustrated construction is ease of access to the strips 122, 124. They are visible above the vial body rim or dispensing opening 126 when the lid 128 is open, and remain exposed above the dispensing opening 126 when the container is full, as well as after strips have been depleted. Yet, the test strips 122, 124 do not interfere with opening and closing the lid 128. Another advantage is that the strips remain standing upright and do not fall over into the sealing locations 136 and 138 when strips are removed.

The illustrated construction optionally provides a longer shelf life for the strips 122, 124 by providing desiccants in various forms, as by two-shot molding of the body 126 to include a desiccant liner, molding internal components of the dispenser 120 from moldable desiccant thermoplastic materials, and including communicating chambers for containing loose or packaged desiccants. One or more of these or other expedients for desiccating the dispenser 120 can be used.

Figure 20:
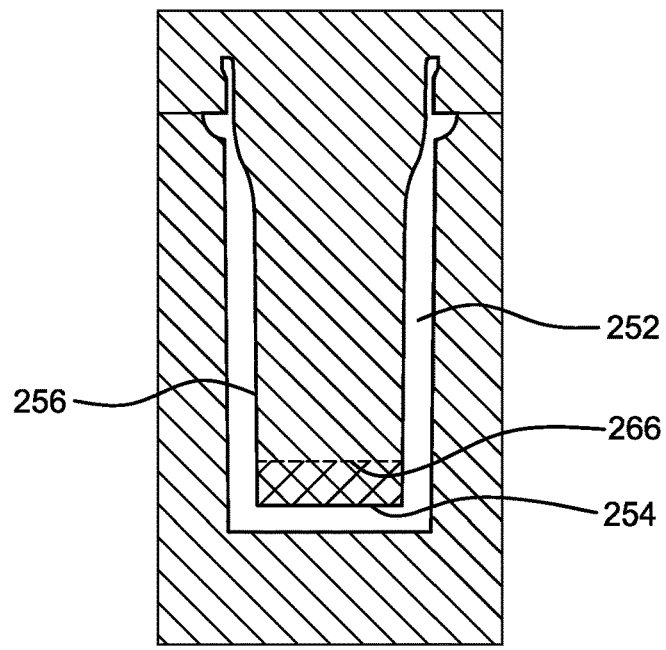
FIG. 20 is a schematic sectional view of a mold cavity for forming the body of a dispenser as shown in FIG. 12.
Figure 21:
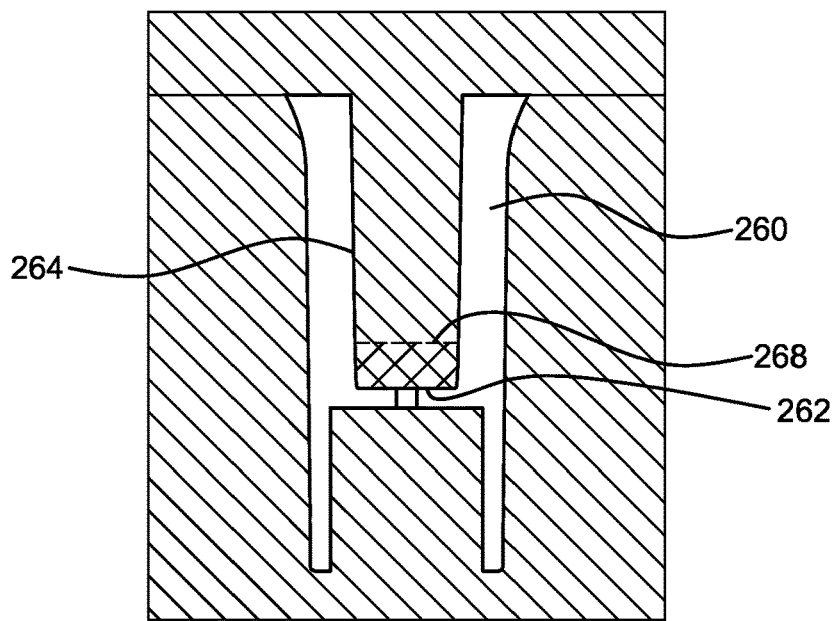
FIG. 21 is a schematic sectional view of a mold cavity for forming the insert of a dispenser as shown in FIG. 12.

Another aspect of the technology, illustrated by FIGS. 12, 20 and 21, is a method of making dispensers such as 120 for dispensing objects such as 124 of varying length. The method allows one to customize a particular dispenser 120 to dispense objects such as 124 of a particular length, presenting the tops 250 of the objects such as 124 at an appropriate height in the dispenser 120.

To carry out the method, a first injection mold cavity 252 is provided as shown in FIG. 20. The first mold cavity 252 is adapted to form a generally tubular body such as the body 126 of FIG. 12. The body 126 has a first platform 146, as previously described, that is formed in the cavity 252 by the projecting end 254 of the core 256, and which locates and supports the lower end 186 of the liner 184 when the dispenser 120 is assembled.

A second injection mold cavity 260 is provided as shown in FIG. 21. The second cavity 260 is adapted to form an insert or liner 184, such a the liner 184 of FIG. 5, sized and configured to fit within the generally tubular body 126 of FIG. 12. The insert 184 has a second platform 150, as shown in FIG. 12 and described above, adapted to support objects such as 124. The second platform is formed by the leading edge 262 of a core 264.

To customize the dispenser 120, at least one of the first and second injection mold cavities 252 and 260 is modified to place the first and second platforms 146 and 150 of the tubular body 126 and the insert 184 in relative axial positions adapted to support objects such as 124 of a specific length on the second platform 150 at a predetermined position relative to the dispensing opening 142.

For example, the position of the first platform 146 in the body 126 can be raised by removing material from the core 256, so its new leading edge 266 is at the position shown in FIG. 20. Alternatively, the core 256 can be replaced by a different core having a different length. Other expedients for accomplishing this customization step are also well known to those skilled in the art. This modification will raise the level of the second platform of a dispenser assembled from the modified body 126 and the insert 184 as shown in FIG. 12.

For another example, the position of the second platform 150 in the insert 184 can be raised by removing material from the core 264, or by other expedients similar to those useful for the cavity 252, so the new leading edge 268 is at the position shown in FIG. 21. This modification will raise the level of the second platform 150 of a dispenser assembled from the body 126 as shown in FIG. 12 and the insert 184 as thus modified.

Further, both of these modifications could be made at the same time, or either one could be used without using the other.

Of course, the opposite modification could be made in either or both cases to lower the position of the second platform 150.

This method allows one to customize the insert 184 to serially adapt for strips 124 of different lengths, presenting each at the ideal height for easy access without interfering with the lid 128. Thus, a variety of different inserts 184 having different dimensions can be used with a particular body 126, depending on the particular strips 124 to be contained and dispensed. Conversely, this method allows one to customize the body 126 to serially adapt for strips 124 of different lengths, presenting each at the ideal height for easy access without interfering with the lid 128. Thus, a variety of different bodies 126 having different dimensions can be used with a particular insert 184, depending on the particular strips 124 to be contained and dispensed.

It will be understood as well, with reference to FIG. 18, that one strip reservoir such as 228 of the insert 184 can be modified using this technique while another strip reservoir 222 retains its original dimensions or is modified to a different degree to suit a strip having a different length. Thus, a very simple and versatile way to customize dispensers 126 for a wide variety of different strips such as 124 has been illustrated.

Figure 23:
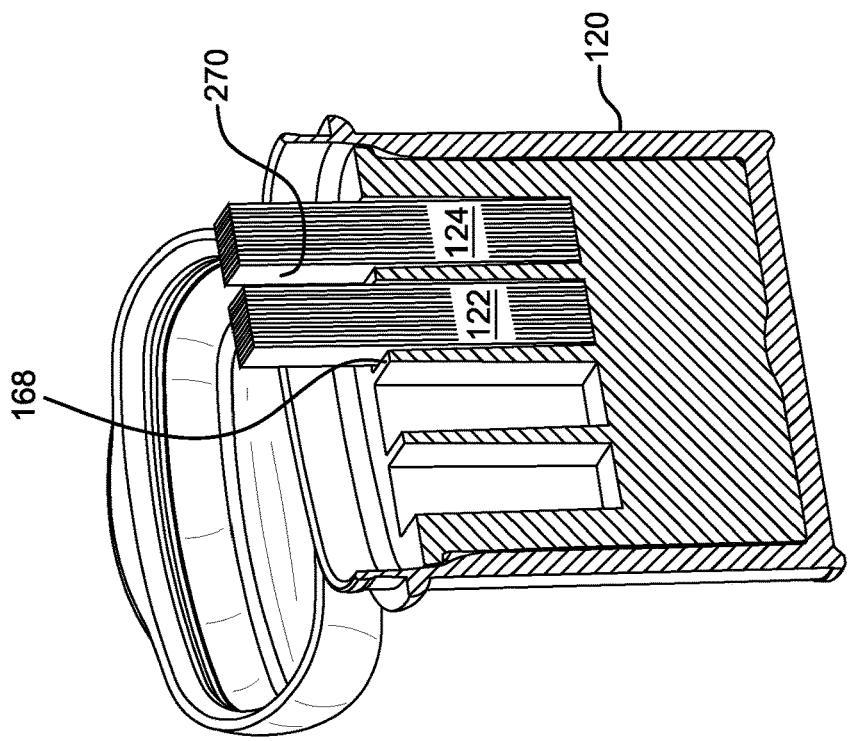
FIG. 23 is a sectional view of an embodiment in which the faces or major surfaces of the strips face the shorter side of the generally oval vial.
Figure 22:
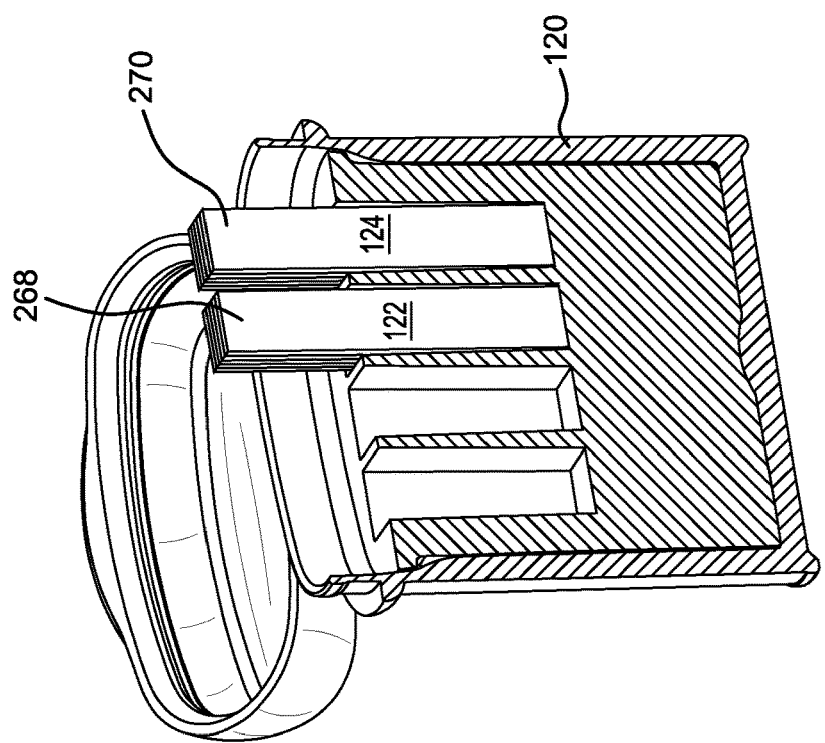
FIG. 22 is a sectional view of an embodiment in which the faces or major surfaces of the strips face the longer side of the generally oval vial.

FIGS. 22 and 23 illustrate that the strips can be oriented in various directions in the dispenser 120. In FIG. 22, the strips are oriented so their major surfaces such as 268 and 270 face one of the longer sides of the dispenser 120. In FIG. 23, the test strips are turned 90 degrees relative to the strips of FIG. 22, so the major surfaces such as 268 and 270 face one of the shorter sides of the dispenser 120. In other words, the dispenser has perpendicular laterally extending first and second axes, and one or more strips of material in at least one of the reservoirs is oriented with its major faces substantially parallel to the first axis, or alternatively the second axis. Other orientations, such as an oblique or diagonal orientation, are also contemplated.

Moisture Ingress Test Method

The following is a suitable method of measuring moisture ingress for determining whether a vessel is waterproof as defined in this specification.

The moisture ingress through the flip-top seal of the container of the present invention is determined over a fifty (50) day period. A total of six (6) containers are used for the study. Two containers, referred to as CONTROL A and CONTROL B, do not contain desiccant. Four other containers, referred to as Samples C, D, E, F, have 2.0 grams of loose molecular sieve (MS) powder placed inside, plus or minus 0.25 grams. The dimensions of the containers are approximately 26.75 mm thick×43.70 mm wide×50.25 mm tall.

The test method can be described as follows: (a) placing two grams plus or minus 0.25 grams of molecular sieve ("MS") into four (4) containers and recording the weight; (b) recording the weight of two of the same containers which do not contain any MS material, which containers are maintained as controls; (c) closing the containers by applying, in a singular motion, a downward pressure upon the container lids or thumb tabs until the rim portions, adjacent to the thumb tabs, contact the inside flat part of the caps also adjacent to the thumb tabs; (d) weighing the six (6) containers and recording their respective weights; (e) placing the closed containers in an environmental chamber maintained at conditions of 80% relative humidity and 22.2° C.; (f) weighing the containers on a daily basis for fifty (50) days, recording the weights of the respective containers, and returning them to the chamber; (g) subtracting the weights recorded in steps (a) and (b) from the current day weight of the respective containers to calculate the moisture ingress of the container in units of micrograms of water; and (h) determining the moisture ingress through the seal by discounting the moisture ingress through the vial, according to the following methodology, calculated on a daily basis:

$N$ is Sample Type $(A-F)$ $Sn$ is Sample Weight Gain=(Current Vial Weight minus Initial Vial Weight at Start of Study)

Ctrl is Average Weight Gain of Control Samples= $(SA+SB)/2$ $TS$ is Average Weight Gain of Test Samples=$(SC+SD+SE+SF)/4$ $MI$ is Moisture Ingress through Seal=$(TS-\text{Ctrl})$.

Working Example: Insert to Improve Seal Integrity of Oval Vial (Container)

Two different groups of oval-section vials with lids, respectively formed in Mold Cavity A and Mold Cavity B, and press-in tubular inserts for each type of vial similar to the inserts forming the surface 58 in FIG. 2 were provided. The tubular inserts were found to reinforce the vials against deflection of the body wall along the minor axis.

The moisture ingress test was run on a group of the vials without an insert, and also on a group of the same types of vials with inserts. The following results were obtained:

Moisture Ingress Results:

|  |  | μg H$_2$O per day | |
| --- | --- | --- | --- |
|  |  | Vial | Vial with insert |
| Mold Cavity A | Best result | 600 | 400 |
|  | Mean Ingress | 716 | 466 |
|  | Std Dev | 90 | 54 |
| Mold Cavity B | Best result | 500 | 380 |
|  | Mean Ingress | 694 | 419 |
|  | Std Dev | 116 | 39 |

In the above test results, the "best result" numbers are the best single vial result of the several vials tested.

The test results show a significant reduction in moisture ingress in the same vials, having the same sealing arrangements, with and without a reinforcement that reduces deflection of the sidewall along the minor axis.

Certain embodiments of the invention have been described in detail in this specification and illustrated by the drawing figures. This invention is not limited, however, to the specific embodiments and features described in the specification. The invention extends to the full scope of the claims as initially or later presented in this specification.

The invention claimed is:

1. A moisture-tight, re-sealable container comprising:
   a body having a sidewall with first and second axially opposed ends, a base, and a dispensing opening axially spaced from the base and adjacent to the second end;
   an interior space disposed within the sidewall and between the base and the dispensing opening;
   an insert within the interior space, at least one elastomeric gasket positioned over the insert, the insert defining a cavity configured to hold one or more test strips, the elastomeric gasket extending over the cavity, the insert being configured to orient the one or more test strips;
   a body sealing surface located on the body and disposed about the dispensing opening;
   a lid configured to seat on the body; and
   a lid sealing surface located on the lid, the body sealing surface and the lid sealing surface being configured to mate to form a seal between the lid and the body when the lid is seated on the body,
   wherein the container is configured to store the one or more test strips such that an exposed end of each of the one or more test strips extends beyond the dispensing opening of the body, and wherein the exposed ends of the test strips are positioned within the lid when the lid is seated on the body without damaging the exposed ends.

2. The container of claim 1, wherein the body is non-round in cross-section.

3. The container of claim 2, wherein the sidewall of the body is tubular and has a cross-section having a major axis and a minor axis, the ratio between the major axis and the minor axis of the sidewall cross-section being a value between 1.1:1 and 10:1, inclusive.

4. The container of claim 3, wherein the insert provides a reinforcement stiffening the body sealing surface against deflection along the minor axis when the lid is seated on the body.

5. The container of claim 4, wherein the insert is made of a desiccant material or contains a desiccant.

6. The container of claim 4, wherein the reinforcement comprises a partition within the interior space.

7. The container of claim 3, wherein the lid comprises a tubular skirt surrounding and depending from said lid sealing surface, a cross-section of the skirt is substantially congruent to the cross-section of the sidewall of the body and at least defining an extension of the sidewall when said lid is seated on the body.

8. The container of claim 1, wherein the lid has a closed surface, and wherein at least a portion of the closed surface is dome-shaped and axially spaced from the entire dispensing opening when the lid is seated on the body.

9. The container of claim 1, wherein the lid and lid sealing surface combine to close the dispensing opening and isolate the interior space from ambient conditions.

10. The container of claim 1, wherein the container has a moisture ingress rate of 100-1000 micrograms per day, at 80% relative humidity and 22.2° C.

11. The container of claim 1, wherein the elastomeric gasket is an annular seal gasket on a top of the insert, the seal gasket surrounding the cavity configured to hold the one or more test strips.

12. The container of claim 1, wherein the insert is secured to the container by an interference fit between the insert and an inner wall of the container.

13. The container of claim 1, wherein the one or more test strips are positioned within the interior space.

14. The container of claim 13, wherein at least a portion of the elastomeric gasket contacts the one or more test strips.

15. The container of claim 14, wherein each of the one or more test strips includes two opposing side surfaces and two opposing face surfaces, the side surfaces extending perpendicularly to the face surfaces, each face surface having a greater surface area than each side surface, the elastomeric gasket contacting each of the one or more test strips on one of the side surfaces thereof.

16. The container of claim 13, wherein at least one of the one or more test strips includes a top surface and an opposing bottom surface, and wherein when the container is in an up-right position, the top surface of the at least one of the one or more test strips extends above the elastomeric gasket and into the lid when the lid is seated on the body.

17. The container of claim 13, wherein at least one of the one or more test strips includes a top surface and an opposing bottom surface, and wherein when the container is in an up-right position, the bottom surface of the at least one of the one or more test strips contacts the insert and the top surface of the one or more test strips extends above the elastomeric gasket and into the lid when the lid is seated on the body.

18. The container of claim 1, wherein the elastomeric gasket includes a sealing surface encircling the one or more test strips.

19. The container of claim 1, wherein no portion of the insert extends above the elastomeric gasket.

20. A moisture-tight, re-sealable container comprising:
a body having a sidewall with first and second axially opposed ends, a base, and a dispensing opening axially spaced from the base and adjacent to the second end;
an interior space disposed within the sidewall and between the base and the dispensing opening;
an insert within the interior space, at least one elastomeric member being positioned over the insert, the insert defining a cavity configured to hold one or more test strips, the elastomeric member extending over the cavity, the insert being configured to orient the one or more test strips;
a body sealing surface located on the body and disposed about the dispensing opening;
a lid configured to seat on the body; and
a lid sealing surface located on the lid, the body sealing surface and the lid sealing surface being configured to mate to form a seal between the lid and the body when the lid is seated on the body,
wherein the container is configured to store the one or more test strips such that an exposed end of each of the one or more test strips is positioned within the lid when the lid is seated on the body without damaging the exposed ends.

21. The container of claim 20, wherein no portion of the insert extends above the elastomeric member.

22. A moisture-tight, re-sealable container, the container comprising:
a body having a sidewall with first and second axially opposed ends, a base at the first end, a dispensing opening axially spaced from the base and adjacent to the second end, a body sealing surface located on the body and disposed about the dispensing opening, an insert positioned within the body, at least one elastomeric member positioned within the body; and
a lid configured to seat on the body, the lid having a lid sealing surface configured to mate with the body sealing surface of the body to form a seal between the lid and the body when the lid is seated on the body,
wherein, when the lid is seated on the body, the combined lid and body form a strip containing space configured to hold one or more test strips, the strip containing space comprising a cavity formed by the insert and a void formed by the lid, the void being above the cavity, the at least one elastomeric member extending into the strip containing space,
wherein at least a portion of the elastomeric member is configured to contact the one or more test strips, and
wherein an exposed end of each of the one or more test strips is configured to be positioned within the void when the lid is seated on the body without damaging the exposed ends.

23. The container of claim 22, wherein the one or more test strips are positioned within an interior space of the container and wherein at least a portion of the elastomeric member contacts the one or more test strips.

24. The container of claim 23, wherein at least one of the one or more test strips includes a top surface and an opposing bottom surface, and wherein when the container is in an up-right position, the top surface of the at least one of the one or more test strips extends above the elastomeric member and into the lid when the lid is seated on the body.

* * * * *